US010077294B2

(12) United States Patent
Rebollo Garcia et al.

(10) Patent No.: US 10,077,294 B2
(45) Date of Patent: Sep. 18, 2018

(54) PEPTIDE INHIBITORS OF TEAD/YAP-TAZ INTERACTION

(71) Applicants: UNIVERSITE PIERRE ET MARIE CURIE (PARIS 6), Paris (FR); INSTITUT CURIE, Paris (FR)

(72) Inventors: Angelita Rebollo Garcia, Paris (FR); Fariba Nemati, Paris (FR); Didier Decaudin, Verrieres le Buisson (FR)

(73) Assignees: UNIVERSITE PIERRE ET MARIE CURIE (PARIS 6), Paris (FR); INSTITUT CURIE, Paris (FR)

( * ) Notice: Subject to any disclaimer, the term of this patent is extended or adjusted under 35 U.S.C. 154(b) by 0 days.

(21) Appl. No.: 15/031,754

(22) PCT Filed: Nov. 4, 2014

(86) PCT No.: PCT/IB2014/065794
§ 371 (c)(1),
(2) Date: Apr. 25, 2016

(87) PCT Pub. No.: WO2015/063747
PCT Pub. Date: May 7, 2015

(65) Prior Publication Data
US 2016/0264636 A1    Sep. 15, 2016

(30) Foreign Application Priority Data
Nov. 4, 2013  (EP) .................................... 13306512

(51) Int. Cl.
C07K 14/47 (2006.01)
C07K 7/08 (2006.01)
A61K 38/00 (2006.01)

(52) U.S. Cl.
CPC ............ C07K 14/4703 (2013.01); C07K 7/08 (2013.01); *A61K 38/00* (2013.01); *C07K 2319/10* (2013.01); *C07K 2319/23* (2013.01)

(58) Field of Classification Search
CPC ............. C07K 7/00; C07K 9/00; C07K 14/00
See application file for complete search history.

(56) References Cited

U.S. PATENT DOCUMENTS

2011/0027186 A1*  2/2011  Hong .................... C07K 16/18
                                                            424/9.2

FOREIGN PATENT DOCUMENTS

| CN | 102136042 A | 7/2011 | |
| WO | WO 0207752 A2 * | 1/2002 | ......... C12N 15/8509 |
| WO | 2009/045179 A1 | 4/2009 | |
| WO | 2013/098337 A1 | 7/2013 | |
| WO | 2013/098339 A1 | 7/2017 | |

OTHER PUBLICATIONS

Tian et al., "Structural and functional analysis of the YAP-binding domain of human TEAD2", PNAS, 2010, 7293-7298.*
CN102136042, 2011; Description; English Translation; pp. 1-72.*
UniProt Database Accession No. Q15562, Oct. 16, 2013.
B. Zhao et al: "TEAD mediates YAP-dependent gene induction and growth control", Genes & Development, vol. 22, No. 14, Jul. 15, 2008 (Jul. 15, 2008), pp. 1962-1971.
H. Zhang et al: "TEAD Transcription Factors Mediate the Function of TAZ in Cell Growth and Epithelial-Mesenchymal Transition", Journal of Biological Chemistry, vol. 284, No. 20, Mar. 26, 2009 (Mar. 26, 2009), pp. 13355-13362.
S. W. Chan et al: "TEADs Mediate Nuclear Retention of TAZ to Promote Oncogenic Transformation", Journal of Biological Chemistry, vol. 284, No. 21, Mar. 26, 2009 (Mar. 26, 2009), pp. 14347-14358.
Q.-Y. Lei et al: "TAZ Promotes Cell Proliferation and Epithelial-Mesenchymal Transition and Is Inhibited by the Hippo Pathway", Molecular and Cellular Biology, vol. 28, No. 7, Apr. 1, 2008 (Apr. 1, 2008), pp. 2426-2436.

* cited by examiner

Primary Examiner — Lianko G Garyu
(74) Attorney, Agent, or Firm — Arrigo, Lee, Guttman & Mouta-Bellum LLP

(57) ABSTRACT

The invention relates to an isolated peptide inhibitor of the interaction between the TEAD and YAP or TAZ proteins and a derived chimeric peptide linked to a cell-penetrating peptide. These peptides which have a cytotoxic activity are useful, in particular for the treatment of hyperproliferative disorders such as cancer.

2 Claims, 13 Drawing Sheets

Figure 1A:
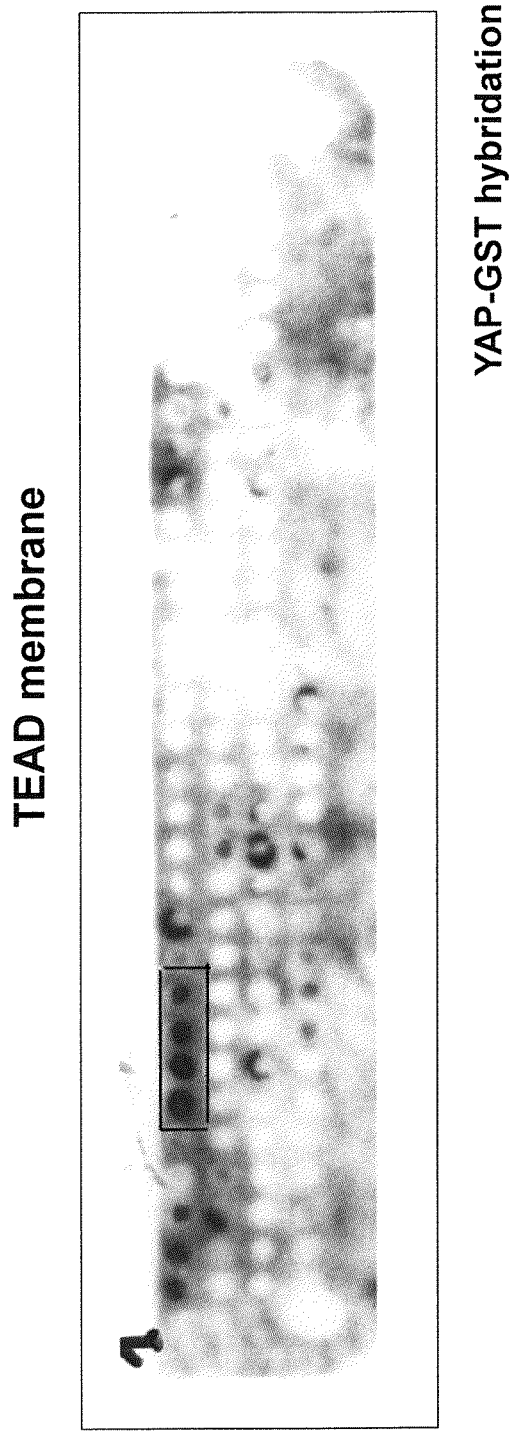

Specification includes a Sequence Listing.

TEAD: RLQLVEFSAFVEPPDAVD (SEQ ID NO: 1)

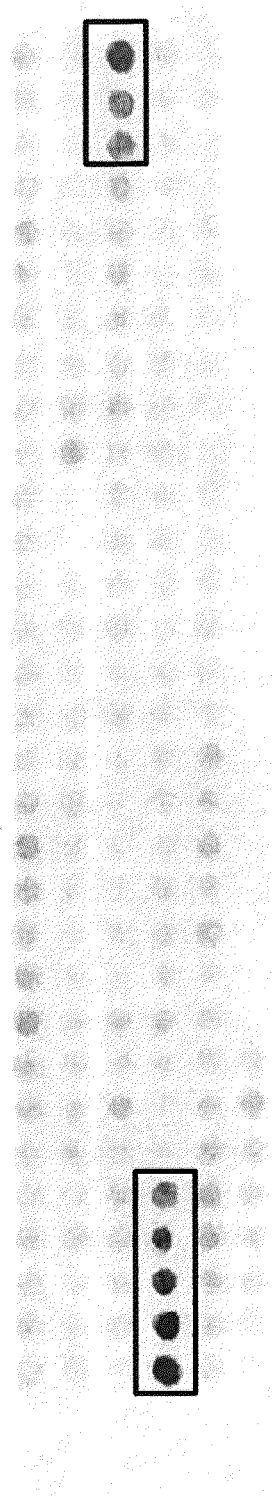
TAZ: PPHAFFLVKFWADLNWGPSGEEAGAG (SEQ ID NO: 2)
FIGURE 1B

Table III: Cytotoxicity of TAZ peptide in combination with chemotherapy

| Drugs | A549 | | H1299 | | H1650 | | H1975 | | HBEC wt | | HBEC RasV12 | |
|---|---|---|---|---|---|---|---|---|---|---|---|---|
| | Cell viability (%) | p | Cell viability (%) | p | Cell viability (%) | p | Cell viability (%) | p | Cell viability (%) | p | Cell viability (%) | p |
| HPCD10 % vs TAZ | -38 | 0.05 | -24.71 | 0.05 | -30.68 | 0.05 | -49.35 | 0.05 | -58.16 | 0.05 | -89.9 | 0.05 |
| NaCl vs Docetaxel | 11.73 | 0.05 | -10.53 | 0.05 | 23.41 | 0.05 | 5.931 | 0.35 | 25.93 | 0.05 | 15.19 | 0.05 |
| NaCl vs Cisplatin | -37.43 | 0.05 | -57.12 | 0.05 | -55.41 | 0.05 | -76.57 | 0.05 | -21.45 | 0.05 | -44.42 | 0.05 |
| Glucose 5% vs Tarceva | -52.89 | 0.05 | -39.83 | 0.05 | -47.11 | 0.05 | -49.68 | 0.05 | -15.63 | 0.1 | -4.596 | 0.35 |
| Docetaxel+TAZ vs Docetaxel | -49.07 | 0.05 | -23.98 | 0.05 | -55.64 | 0.05 | -52.44 | 0.05 | -87.57 | 0.05 | -91.24 | 0.05 |
| Cisplatin+ TAZ vs Cisplatin | -19.83 | 0.05 | 25.52 | 0.05 | -2.621 | 0.1 | 26.72 | 0.05 | -45.43 | 0.05 | -36.13 | 0.05 |
| Tarceva+ TAZ vs Tarceva | -17.14 | 0.05 | -15.53 | 0.05 | -15.51 | 0.05 | -15.34 | 0.05 | -49.87 | 0.05 | -75.46 | 0.05 |

FIGURE 9

Table IV: Cytotoxicity of TEAD peptide in combination with chemotherapy

| Drugs | A549 | | H1299 | | H1650 | | H1975 | | HBEC wt | | HBEC RasV12 | |
|---|---|---|---|---|---|---|---|---|---|---|---|---|
| | Cell viability (%) | p | Cell viability (%) | p | Cell viability (%) | p | Cell viability (%) | p | Cell viability (%) | p | Cell viability (%) | p |
| Glucose 5% vs TEAD | 3.124 | 0.2 | -12.44 | 0.05 | -25.3 | 0.05 | -20.23 | 0.05 | -15.41 | 0.05 | -36.65 | 0.05 |
| NaCl vs Docetaxel | -49.02 | 0.05 | -72.38 | 0.05 | -41.32 | 0.05 | -92.17 | 0.05 | -54.02 | 0.05 | -88.64 | 0.05 |
| NaCl vs Cisplatin | -60.45 | 0.05 | -73.62 | 0.05 | -77.26 | 0.05 | -85.91 | 0.05 | -77.04 | 0.05 | -55.51 | 0.05 |
| Glucose 5% vs Tarceva | -60.75 | 0.05 | -60.68 | 0.05 | -38.72 | 0.05 | -77.63 | 0.05 | -55.15 | 0.05 | -25.67 | 0.05 |
| Docetaxel+TEAD vs Docetaxel | 12.24 | 0.05 | 4.686 | 0.05 | -1.734 | 0.45 | 10.64 | 0.1 | 8.283 | 0.2 | 16.1 | 0.05 |
| Cisplatin+ TEAD vs Cisplatin | 10.31 | 0.05 | 4.66 | 0.1 | 12.84 | 0.05 | 3.859 | 0.2 | -2.179 | 0.1 | -25.87 | 0.05 |
| Tarceva+ TEAD vs Tarceva | 4.072 | 0.05 | 11.65 | 0.05 | -8.019 | 0.1 | 13.62 | 0.35 | -21.67 | 0.05 | -43.69 | 0.05 |

FIGURE 10

Table V: Cytotoxicity of YAP peptide in combination with chemotherapy

| Drugs | A549 | | H1299 | | H1650 | | H1975 | | HBEC wt | | HBEC RasV12 | |
|---|---|---|---|---|---|---|---|---|---|---|---|---|
| | Cell viability (%) | p | Cell viability (%) | p | Cell viability (%) | p | Cell viability (%) | p | Cell viability (%) | p | Cell viability (%) | p |
| Glucose 5% vs YAP | -23.19 | 0.05 | -40.21 | 0.05 | -45.14 | 0.05 | -26.22 | 0.05 | -60.73 | 0.05 | -72.88 | 0.05 |
| NaCl vs Docetaxel | -39.31 | 0.05 | -89.07 | 0.05 | 0.1681 | 0.3 | -79.23 | 0.05 | -2.578 | 0.35 | -95.93 | 0.05 |
| NaCl vs Cisplatin | -57.64 | 0.05 | -95.42 | 0.05 | -83.01 | 0.05 | -97.93 | 0.05 | -77.96 | 0.05 | -89.58 | 0.05 |
| Glucose 5% vs Tarceva | -67.3 | 0.05 | -61.14 | 0.05 | -53.13 | 0.05 | -56.6 | 0.05 | -37.28 | 0.05 | 0.2682 | 0.45 |
| Docetaxel+YAP vs Docetaxel | -4.286 | 0.05 | 2.885 | 0.2 | -51.2 | 0.05 | -1.23 | 0.05 | -53.37 | 0.05 | -1.487 | 0.05 |
| Cisplatin+ YAP vs Cisplatin | -14.62 | 0.05 | -2.22 | 0.1 | -2.413 | 0.2 | -1.266 | 0.05 | -14.32 | 0.05 | -9.699 | 0.05 |
| Tarceva+ YAP vs Tarceva | -5.627 | 0.05 | 0.6546 | 0.45 | -26.24 | 0.05 | 17.88 | 0.05 | -24.55 | 0.05 | -59.88 | 0.05 |

FIGURE 11

Table VI: Cytotoxicity of TAZ peptide in combination with YAP peptide

| Drugs | A549 | | H1299 | | H1650 | | H1975 | | HBEC wt | | HBEC RasV12 | |
|---|---|---|---|---|---|---|---|---|---|---|---|---|
| | Cell viability (%) | p | Cell viability (%) | p | Cell viability (%) | p | Cell viability (%) | p | Cell viability (%) | p | Cell viability (%) | p |
| HPCD 10% vs TAZ | -7.835 | 0.05 | -8.413 | 0.05 | -2.439 | 0.2 | -13.21 | 0.05 | -66.15 | 0.05 | -53.02 | 0.05 |
| HPCD 10% vs YAP | -10.25 | 0.05 | -13.8 | 0.35 | -4.488 | 0.05 | -5.766 | 0.05 | -41.35 | 0.05 | -44.98 | 0.05 |
| TAZ+YAP vs TAZ | -9.003 | 0.05 | -16.72 | 0.05 | -24.59 | 0.05 | -3.522 | 0.05 | -28.28 | 0.05 | -27.88 | 0.05 |
| TAZ+ YAP vs YAP | -6.592 | 0.1 | -11.33 | 0.05 | -22.54 | 0.05 | -10.96 | 0.05 | -53.08 | 0.05 | -35.91 | 0.05 |

FIGURE 12

Table IX: Cytotoxicity of TAZ peptide in combination with chemotherapy

| Drugs | ES2 | | SKOV3 | | IGROV | | OVCAR8 | |
|---|---|---|---|---|---|---|---|---|
| | Cell viability (%) | p | Cell viability (%) | p | Cell viability (%) | p | Cell viability (%) | p |
| HPCD 10% vs TAZ (10µM) | -46.33 | 0.05 | -26.64 | 0.05 | -39.39 | 0.05 | -18.7 | 0.05 |
| HPCD 10% vs TAZ (25µM) | -57.44 | 0.05 | -36.09 | 0.05 | -34 | 0.05 | -24.69 | 0.05 |
| NaCl vs Carbo+Pacli | -88.62 | 0.05 | -34.97 | 0.05 | -64.32 | 0.05 | -76.46 | 0.05 |
| Carbo+Pacli +TAZ (10µM) vs Carbo+Pacli | -12.39 | 0.05 | -4.425 | 0.1 | -5.03 | 0.05 | -19.25 | 0.05 |
| Carbo+Pacli +TAZ (25µM) vs Carbo+Pacli | -13.64 | 0.05 | -12.89 | 0.05 | -2.338 | 0.05 | -23.96 | 0.05 |

FIGURE 13

PEPTIDE INHIBITORS OF TEAD/YAP-TAZ INTERACTION

The invention relates to peptide inhibitors of the interaction between the TEAD and YAP or TAZ proteins, and to derived chimeric peptides linked to a cell-penetrating peptide. These peptides which have a cytotoxic activity are useful, in particular for the treatment of hyperproliferative disorders such as cancer.

The Hippo signalling pathway is a major regulator of cell proliferation and apoptosis, which is conserved from *drosophila* to mammals (Vassilev et al., Genes and Development, 2001, 15, 1229-1241; Zeng and Hong, Cancer Cell, 2008, 13, 188-192). The core of the pathway consists of a cascade of kinases (Hippo-MST1-2 being upstream of Lats 1-2 and NDR1-2) leading to the phosphorylation of two transcriptional co-activators, YAP (Yes-Associated Protein) and TAZ (Transcription co-activator with PDZ binding motif or tafazzin; Zhao et al., Cancer Res., 2009, 69, 1089-1098; Lei et al., Mol. Cell. Biol., 2008, 28, 2426-2436).

Upon phosphorylation, these two proteins are retained into the cytosol via interaction with the 14-3-3 proteins and their transcriptional activity is therefore inhibited. When the upstream kinases are inactive, YAP and TAZ are not phosphorylated and translocate to the nucleus. Both proteins are unable to bind DNA directly, but need physical interactions with DNA binding proteins to exert their transcriptional activity. Various YAP/TAZ nuclear DNA-binding partners have been identified, the most important in driving cell proliferation being the TEAD transcription factors (TEA domain family members or transcription enhancer factors (TEF)). There are four closely related human TEAD proteins (hTEAD1-4) containing an N-terminal DNA-binding TEA domain and a C-terminal YAP-binding domain (positions 40-104 and 217 to 447, respectively of hTEAD2 amino acid sequence by reference to UniProtKB/Swiss-Prot Q15562.2). The YAP-binding domain has an extensive YAP-binding surface involving at least nine critical residues (E267, I274, K277, L299/K301, W303, E404/N405, V427/E429, Y442 and L444) spread throughout the YAP-binding domain and forming a surface exposed pocket. YAP has an N-terminal TEAD-binding domain and a C-terminal transcriptional activation domain (positions 48 to 102 and 292 to 488, respectively of hYAP amino acid sequence by reference to UniProtKB/Swiss-Prot P46937.2 or NCBI NP_001123617.1). A 40mer YAP$^{61-100}$ peptide is sufficient to bind TEAD, whereas a smaller peptide YAP$^{67-97}$ is not able to bind TEAD (Tian et al., PNAS, 2010, 107, 7293-7298).

The Hippo pathway activity is modulated by various cellular inputs such as cell-cell contact, actin cytoskeleton status, mechanical or metabolic cues. Several proteins exert regulatory function on the Hippo pathway. Notably, the activity of MST1-2 is regulated by the tumor suppressors NF2 and RASSF1A as well as Kibra, whereas Lats1-2 kinases are under the control of Salvador (sv)/Mob1 complex.

The Hippo signalling pathway is a crucial regulator of animal development, organ size control and stem cell regulation. Hence, not surprisingly, evidences of its involvement in cancer development have accumulated over the past few years (Review in Harvey et al., Nat. Rev. Cancer, 2013, 13, 246-257; Zhao et al., Genes Dev. 2010, 24, 862-874). In vitro, the overexpression of YAP or TAZ in mammary epithelial cells induces cell transformation, through interaction of both proteins with the TEAD family of transcription factors. Increased YAP/TAZ transcriptional activity induces oncogenic properties such as epithelial-mesenchymal transition and was also shown to confer stem cells properties to breast cancer cells. In vivo, in mouse liver, the overexpression of YAP or the genetic knockout of its upstream regulators MST1-2 triggers the development of hepatocellular carcinomas. Furthermore, when the tumor suppressor NF2 is inactivated in the mouse liver, the development of hepatocellular carcinomas can be blocked completely by the co-inactivation of YAP. Finally, a recent study on several major types of cancers has shown a frequent pattern of YAP nuclear accumulation whereas methylation or mutations of RASSF1A, Lats2, MST1-2 have been also reported in various human cancers.

Overall, it appears that the deregulation of the Hippo tumor suppressor pathway is emerging as a major event in the development of a wide range of malignancies, including with no limitations, lung (NSCLC; Zhou et al., Oncogene, 2011, 30, 2181-2186; Wang et al., Cancer Sci., 2010, 101, 1279-1285), breast (Chan et al., Cancer Res., 2008, 68, 2592-2598; Lamar et al., Proc. Natl. Acad. Sci. USA, 2012; 109, E2441-E2250; Wang et al., Eur. J. Cancer, 2012, 48, 1227-1234), head and neck (Gasparotto et al., Oncotarget., 2011, 2, 1165-1175; Steinmann et al., Oncol. Rep., 2009, 22, 1519-1526), colon (Angela et al., Hum. Pathol., 2008, 39, 1582-1589; Yuen et al., PLoS One, 2013, 8, e54211; Avruch et al., Cell Cycle, 2012, 11, 1090-1096), ovarian (Angela et al., Hum. Pathol., 2008, 39, 1582-1589; Chad et al., Cancer Res., 2010, 70, 8517-8525; Hall et al., Cancer Res., 2010, 70, 8517-8525), liver (Jie et al., Gastroenterol. Res. Pract., 2013, 2013, 187070; Ahn et al., Mol. Cancer. Res., 2013, 11, 748-758; Liu et al., Expert. Opin. Ther. Targets, 2012, 16, 243-247), brain (Orr et al., J Neuropathol. Exp. Neurol. 2011, 70, 568-577; Baia et al., Mol. Cancer Res., 2012, 10, 904-913; Striedinger et al., Neoplasia, 2008, 10, 1204-1212) and prostate (Zhao et al., Genes Dev., 2012, 26, 54-68; Zhao et al., Genes Dev., 2007, 21, 2747-2761) cancers, mesotheliomas (Fujii et al., J. Exp. Med., 2012, 209, 479-494; Mizuno et al., Oncogene, 2012, 31, 5117-5122; Sekido Y., Pathol. Int., 2011, 61, 331-344), sarcomas (Seidel et al., Mol. Carcinog., 2007, 46, 865-871) and leukemia (Jimenez-Velasco et al., Leukemia, 2005, 19, 2347-2350). Hence, pharmacological targeting of the Hippo cascade is likely to represent a valuable approach for the treatment of cancers that harbour functional alterations of this pathway.

Therefore, to develop new targeted therapeutic strategies for the treatment of cancer, there is a need for specific inhibitors of the Hippo signalling pathway.

The inventors have evaluated a therapeutic approach based on the inhibition of the activity of the Hippo pathway effectors YAP and TAZ. To do so, they have designed peptides which inhibit the interaction between TEAD factors and YAP or TAZ proteins and chimeric peptides comprising a cell penetrating peptide linked to such peptide inhibitor. Surprisingly, they have found that small peptides derived from YAP, TAZ or TEAD proteins were efficient inhibitors of the TEAD/YAP-TAZ interaction. They have demonstrated the efficacy of this strategy on cellular tumor models of three cancers featuring the inactivation of genes coding for key members of the Hippo pathway.

Therefore, the invention provides a peptide inhibitor of the interaction between TEAD and YAP or TAZ proteins.

The peptide inhibitor of the invention which induces cell toxicity, including the induction of apoptosis, is useful for inhibiting cell proliferation in vitro and in vivo, in particular for treating hyperproliferative diseases, such as cancer. The peptide inhibitor of the invention which binds to TEAD, YAP or TAZ protein and disrupts the interaction between TEAD and YAP or TAZ proteins is also useful as in vitro diagnostic reagent, drug screening reagent and research tool.

The peptide inhibitor of the invention is an isolated, recombinant or synthetic, peptide.

The properties of the peptide can be readily verified by technique known to those skilled in the art such as those described in the examples of the present application.

In the following description, the standard one letter amino acid code is used.

In one embodiment, the peptide inhibitor binds to a TEAD, YAP or TAZ protein. The peptide inhibitor derives advantageously from the binding site of TEAD to YAP or TAZ or of YAP or TAZ to TEAD. Since the Hippo pathway is well conserved in animals, the peptide can derive from mammal TEAD, YAP or TAZ proteins or their homologs found in other species. The peptide inhibitor derives advantageously from a mammal TEAD, YAP or TAZ protein, more advantageously human TEAD1, TEAD2, TEAD3 or TEAD4, even more advantageously human TEAD2, human YAP or human TAZ protein.

Preferably, the peptide inhibitor is a peptide comprising or consisting of one of the following amino acid sequences:

a) RLQLVEFSAFVEPPDAVD (SEQ ID NO: 1) corresponding to the binding site of TEAD to YAP, b) PPHAFFLVKFWADLNWGPSGEEAGAG (SEQ ID NO: 2) corresponding to the binding site of TEAD to TAZ, c) KTANVPQTVPMRLRKLPD (SEQ ID NO: 3) corresponding to the binding site of YAP to TEAD, or d) an amino acid sequence deriving from a sequence in a), b) or c) by a N- and/or C-terminal deletion of 1 to 4 (1, 2, 3 or 4) amino acids, preferably of 1 or 2 amino acids, or a functional variant thereof.

The peptide of SEQ ID NO: 1 corresponds to positions 227 to 244 of human TEAD2 amino acid sequence by reference to UniProtKB/Swiss-Prot Q15562.2.

The peptide of SEQ ID NO: 2 corresponds to positions 293 to 318 of human TEAD2 amino acid sequence by reference to UniProtKB/Swiss-Prot Q15562.2.

The peptide of SEQ ID NO: 3 corresponds to positions 76 to 93 of human YAP amino acid sequence by reference to UniProtKB/Swiss-Prot P46937.2 or NCBI NP_001123617.1.

"Functional" with respect to a peptide of the invention refers to a peptide which is able to bind to a TEAD, YAP or TAZ protein and prevent TEAD/YAP-TAZ interaction, and thereby induce cell toxicity including the induction of apoptosis, and inhibit cell proliferation.

Functional variants include natural variants resulting from gene polymorphism as well as artificial variants. Functional variants are derived from wild-type amino acid sequences by the introduction of one or more mutations (deletion, insertion, and/or substitution) at specific amino acid positions.

A functional variant comprises an amino acid sequence which is "substantially homologous" or "substantially similar" to the sequence of the reference peptide from which it is derived. Two amino acid sequences are "substantially homologous" or "substantially similar" when one or more amino acid residues are replaced by a biologically similar residue or when the sequences are at least 80% identical or 90% similar.

The percent amino acid sequence identity/similarity is defined as the percent of amino acid residues in a Compared Sequence that are identical/similar to the Reference Sequence after aligning the sequences and introducing gaps if necessary, to achieve the maximum sequence identity. The Percent identity is then determined according to the following formula: Percent identity=100×[1−(C/R)], wherein C is the number of differences between the Reference Sequence and the Compared sequence over the entire length of the Reference Sequence, wherein (i) each amino acid in the Reference Sequence that does not have a corresponding aligned amino acid in the Compared Sequence, (ii) each gap in the Reference Sequence, and (iii) each aligned amino acid in the Reference Sequence that is not identical/similar to an amino acid in the Compared Sequence constitutes a difference; and R is the number amino acids in the Reference Sequence over the length of the alignment with the Compared Sequence with any gap created in the Reference Sequence also being counted as an amino acid.

Alignment for purposes of determining percent amino acid sequence identity can be achieved in various ways known to a person of skill in the art, for instance using publicly available computer software such as BLAST (Altschul et al., J. Mol. Biol., 1990, 215, 403-), FASTA, the GCG (Genetics computer Group, Program Manual for the GCG Package, version 7, Madison, Wis.) pileup program, or any of the programs known in the art. When using such software, the default parameters, e.g., for gap penalty and extension penalty, are preferably used. For amino acid sequences, the BLASTP program uses as default a word length (W) of 3 and an expectation (E) of 10.

Conservative substitution refers to the substitution of one amino acid with another, without altering the overall conformation and function of the peptide, including but not limited to the replacement of an amino acid with one which has similar chemical or physical properties (size, charge or polarity), which generally does not modify the functional properties of the protein. Amino acids with similar properties are well known in the art. A non-limitative example of conservative substitution(s) comprises the five following groups: Group 1-small aliphatic, nonpolar or slightly polar residues (A, S, T, P, G); Group 2-polar, negatively charged residues and their amides (D, N, E, Q); Group 3-polar, positively charged residues (H, R, K); Group 4-large aliphatic, nonpolar residues (M, L, I, V, C); and Group 5-large, aromatic residues (F, Y, W). Alternative, examples of conservative substitutions are known in the art.

The functional variant comprises or consists advantageously of an amino acid sequence which is at least 80%, 85%, 90% or 95% to SEQ ID NO: 1, 2 or 3 or a fragment thereof as defined above. More advantageously, the functional variant derives from SEQ ID NO: 1, 2 or 3 by one or more conservative substitutions.

In some embodiments, the functional variant comprises or consists of SEQ ID NO: 38. SEQ ID NO: 38 is derived from SEQ ID NO: 2 by a Leucine to Valine substitution in position 7 and a Valine to Leucine substitution in position 8 of SEQ ID NO: 2.

Preferably, the peptide inhibitor consists of less than 100 amino acids, more preferably less than 70, 65, 60, 55, 50 or 45 amino acids, even more preferably less than 40, 35 or 30 amino acids. In some more preferred embodiments, the peptide inhibitor consists of less than 25 or 20 amino acids.

Another aspect of the invention relates to a fusion or chimeric peptide deriving from the peptide inhibitor as described above.

The fusion or chimeric peptide comprises an amino acid sequence fused to the N-terminal and/or C-terminal end(s) of the peptide inhibitor. The length of the chimeric peptide is not critical to the invention as long as the peptide is functional. The peptide inhibitor is fused to one or more other protein/peptide moieties including those which allow the purification, detection, immobilization, and/or cellular targeting of the protein of the invention, and/or which increase the affinity for TAZ, TEAD or YAP, the bioavailability, the production in expression systems and/or stability of said protein. These moieties may be selected from: (i) a cell-penetrating moiety, (ii) a labeling moiety such as a fluorescent protein (GFP and its derivatives, BFP and YFP), (iii) a reporter moiety such as an enzyme tag (luciferase, alkaline phosphatase, glutathione-S-transferase (GST), β-galactosidase), (iv) a binding moiety such as an epitope tag (polyHis6, FLAG, HA, myc.), a DNA-binding domain, a hormone-binding domain, a poly-lysine tag for immobilization onto a support, (v) a stabilization moiety, and (vi) a targeting moiety for addressing the chimeric protein to a specific cell type or cell compartment. In addition, the peptide inhibitor may be separated from the peptide/protein moiety by a linker which is long enough to avoid inhibiting interactions between the peptide inhibitor and the protein/peptide moiety. The linker may also comprise a recognition site for a protease, for example, for removing affinity tags and stabilization moieties from the purified chimeric protein according to the present invention.

In one embodiment, the chimeric peptide comprises the peptide inhibitor linked to at least one cell-penetrating peptide. In particular embodiments, the peptide inhibitor is linked to two, three or more cell-penetrating peptides. The peptide inhibitor is advantageously fused to the C-terminus of the cell-penetrating peptide.

Cell-penetrating peptides (CPP), also known as protein transduction domains (PTDs), membrane translocation sequences (MTSs), transport peptides, carrier peptides or Trojan peptides are well-known in the art. CPPs are able to translocate into cells (including the cytoplasm and organelles such as mitochondria or the nucleus) at significantly higher levels than passive diffusion, without causing substantial membrane damage, and can be used as vectors of other molecules when linked to them.

The cell-penetrating peptide may be one of those described in WO 03/011898, WO 2004/011595, WO 2010/112471, WO 2012/042038, WO 2013/098337, Guergnon et al., Mol. Pharmacol., 2006, 69, 1115-1124; Fonseca et al., Avanced Drug Delivery Reviews, 2009, 61, 953-964; Nakase et al., Journal of Controlled Release, 2012, 159, 181-188; Bolhassani A., Biochimica et Biophysica Acta, 2011, 1816, 232-246; Milleti F., Drug Discovery Today, 2012, 17, 850-860; Aroui et al., Cancer Letters, 2009, 285, 28-38.

The cell-penetrating peptide is advantageously a short peptide, preferably of less than 40 amino acids.

In a particular embodiment, the cell-penetrating peptide comprises or consists of:

a) $X_1$-KKKIK-Ψ-EI-$X_2$-$X_3$ (SEQ ID NO: 4), wherein $X_1$ is K, VK or is absent; $X_2$ is K, KI or is absent, $X_3$ is a sequence of 1 to 4 amino acids or is absent and Ψ is any amino acid; the cell-penetrating peptide is advantageously $X_1$-KKKIK-Ψ-EI-$X_2$ (SEQ ID NO: 5), preferably VKKKIK-Ψ-EIKI (SEQ ID NO: 6), more preferably VKKKIKREIKI (SEQ ID NO: 7), VKKKKIKNEIKI (SEQ ID NO: 8), VKKKKIKAEIKI (SEQ ID NO: 9) or VKKKKIKEIKI (SEQ ID NO: 10), even more preferably VKKKIKNEIKI (SEQ ID NO: 8), VKKKKIKAEIKI (SEQ ID NO: 9) or VKKKKIKKEIKI (SEQ ID NO: 10).

b) $(RQKRLI)_3$ (SEQ ID NO: 11), $(RHSRIG)_3$ (SEQ ID NO: 12), RHSRIGIIQQRRTRNG (SEQ ID NO: 13), RHSRIGVTRQRRARNG (SEQ ID NO: 14), RRRRRRRSRGRRRTY (SEQ ID NO: 15), or homologous peptides, or c) a peptide chosen from:
Tat peptide having the sequence:

RKKRRQRRR (SEQ ID NO: 16)

or

YGRKKRRQRRR, (SEQ ID NO: 17)

polyarginine peptide consisting of at least 9 arginines. Preferably 9 ($R_9$; SEQ ID NO: 18) or 11 ($R_{11}$; SEQ ID NO: 19) arginines, HA2-$R_9$ peptide having the sequence:

GLFEAIEGFIENGWEGMIDGWYG-$R_9$, (SEQ ID NO: 20)

penetratin peptide having the sequence:

RQIKIWFQNRRMKWKK, (SEQ ID NO: 21)

Transportan peptide or Antp peptide having the sequence:

GWTLNSAGYLLGKINLKALAALAKKIL, (SEQ ID NO: 22)

Vectocell® peptide originating from human heparin binding proteins and/or anti-DNA antibodies, Maurocalcine peptide having the sequence:

GDCLPHLKLCKENKDCCSKKCKRRGTNIEKRCR, (SEQ ID NO: 23)

decalysine peptide having the sequence:

KKKKKKKKKK ($K_{10}$; (SEQ ID NO: 24)

HIV-Tat derived PTD4 peptide having the sequence:

YARAAARQARA, (SEQ ID NO: 25)

Hepatitis B virus translocation motif (PTM) having the sequence:

PLSSIFSRIGDP, (SEQ ID NO: 26)

$mPrP_{1-28}$ peptide having the sequence:

MANLGYWLLALFVMWTDVGLCKKRPKP, (SEQ ID NO: 27)

POD peptide having the sequence:

GGG$(ARKKAAKA)_4$, (SEQ ID NO: 28)

pVEC peptide having the sequence:

LLIILRRRIRKQAHAHSK, (SEQ ID NO: 29)

EB1 peptide having the sequence:

LIRLWSHLIHIWFQNRRLKWKKK, (SEQ ID NO: 30)

Rath peptide having the sequence:

TPWWRLWTKWHHKRRDLPRKPE, (SEQ ID NO: 31)

CADY peptide having the sequence:

GLWRALWRLLRSLWRLLWRA, (SEQ ID NO: 32)

Histatin 5 peptide having the sequence:

DSHAKRHHGYRKFHEKHHSHRGY (SEQ ID NO: 33)

and $Cyt_{86\text{-}101}$ peptide having the sequence:

KKKEERADLIAYLKKA. (SEQ ID NO: 34)

The CPP as described herein have the capability of inducing cell penetration of a peptide fused to the CPP within 30%, 40%, 50%, 60%, 70%, 80%, 90% or 100% of cells of a given cell culture population, including all integers in between, and allow macromolecular translocation within multiple tissues in vivo upon systemic administration.

Preferably, the peptide construct is selected from the group consisting of:

VKKKKIKAEIKI-RLQLVEFSAFVEPPDAVD, (SEQ ID NO: 35)

VKKKKIKAEIKI-PPHAFFLVKFWADLNWGPSGEEAGAG, (SEQ ID NO: 36)

VKKKKIKAEIKI-KTANVPQTVPMRLRKLPD, (SEQ ID NO: 37)
and

VKKKKIKAEIKI-PPHAFFVLKFWADLNWGPSGEEAGAG. (SEQ ID NO: 39)

In another embodiment, the peptide inhibitor or the chimeric peptide is a modified peptide derived from the preceding peptides by introduction of any modification into one or more amino acid residues, peptide bonds, N- and/or C-terminal ends of the peptide, as long as the modified peptide is functional. These modifications which are introduced into the peptide by the conventional methods known to those skilled in the art, include, in a non-limiting manner: the substitution of a natural amino acid with a non-proteinogenic amino acid (D amino acid or amino acid analog); the modification of the peptide bond, in particular with a bond of the retro or retro-inverso type or a bond different from the peptide bond; the cyclization, and the addition of a chemical group to the side chain or the end(s) of the peptide, in particular for coupling an agent of interest to the protein of the invention. These modifications may be used to label the peptide, and/or to increase its stability or its resistance to proteolysis.

Preferably, the peptide inhibitor or chimeric peptide comprises one or more chemical modifications, more preferably chemical modification(s) which protect the peptide against proteolysis.

The N- and/or C-termini of the peptide are advantageously protected against proteolysis. For instance, the N-terminus is in the form of an acetyl group and/or the C-terminus in the form of an amide group.

Alternatively or additionally, the peptide is protected against proteolysis by internal modifications such as the replacement of at least one —CONH-peptide bond by a (CH2NH) reduced bond, a (NHCO) retro-inverso bond, a (CH2-O) methylene-oxy bond, a (CH2-S) thiomethylene bond, a (CH2CH2) carba bond, a (CO—CH) cetomethylene bond, a (CHOH—CH2) hydroxyethylene bond, a (N—N) bond, a E-alcene bond, or a —CH=CH— bond.

Alternatively or additionally, the peptide is advantageously modified by acetylation, acylation, amidation, cross-linking, cyclization, disulfide bond formation, formation of covalent cross-links, formation of cysteine, formation of pyroglutamate, formylation, gamma-carboxylation, glycosylation, GPI anchor formation, hydroxylation, iodination, methylation, myristylation, oxidation, phosphorylation, and the like.

Alternatively or additionally, the peptide is advantageously composed of amino acids in D configuration, which renders the peptide resistant to proteolysis.

Alternatively or additionally, the peptide is advantageously stabilised by intramolecular crosslinking, by modifying at least two amino acid residues with olefinic side chains, preferably C3-C8 alkenyl chains, more preferably penten-2-yl chains, followed by crosslinking of the chains according to the so-called "stapled-peptide technology" described in Walensky et al., Science, 2004, 305, 1466-1470.

Alternatively or additionally, the peptide is advantageously stabilised by covalent binding to a polyethylene glycol (PEG) molecule, preferably a PEG of 1500 Da or 4000 Da, advantageously bound to their C-terminus or a lysine residue. Such coupling has the advantage to decrease urinary clearance and therapeutic doses and increase half-life in blood plasma.

Alternatively or additionally, the peptide is advantageously stabilised and its half-life increased by incorporation into a biodegradable and biocompatible polymer material for drug delivery system forming microspheres, such as for instance poly(D, L-lactide-co-glycolide (PLGA) and nanoparticles. Yet another aspect of the invention relates to an isolated polynucleotide encoding the peptide inhibitor or chimeric peptide.

The polynucleotide is a synthetic or recombinant DNA, RNA or combination thereof, either single- and/or double-stranded. The polynucleotide is encoding the peptide in expressible form, i.e., it is a nucleic acid molecule which, upon expression in a cell or a cell-free system results in a functional peptide.

Preferably the polynucleotide comprises a coding sequence which is optimized for the host in which the peptide is expressed.

In another preferred embodiment, the polynucleotide is inserted in a vector. Preferably, said recombinant vector is an expression vector capable of expressing said polynucleotide when transfected or transformed into a host cell such as a prokaryotic or eukaryotic cell. The polynucleotide is inserted into the expression vector in proper orientation and correct reading frame for expression. Preferably, the polynucleotide is operably linked to at least one transcriptional regulatory sequence and, optionally to at least one translational regulatory sequence. Recombinant vectors include usual vectors used in genetic engineering and gene therapy including for example plasmids and viral vectors, such as for example lentivirus and adenovirus vectors.

Another aspect of the present invention relates to the use of a peptide (peptide inhibitor or derived chimeric peptide), polynucleotide, and/or vector as described herein for inhibiting cell proliferation in vitro.

Another aspect of the present invention relates to a peptide (peptide inhibitor or derived chimeric peptide), polynucleotide, and/or vector as described herein as a medicament. The medicament is useful for inhibiting cell proliferation.

Therefore, another aspect of the present invention relates to a peptide, polynucleotide, and/or vector as described herein, for use in treating hyperproliferative disorders, in particular cancer, preferably in a human patient.

The peptide, polynucleotide, and/or vector as described herein are useful for treating tumors, in particular malignant tumors and preventing or treating metastasis.

More particularly, the peptide, polynucleotide, and/or vector as described herein are useful in the treatment of cancers which exhibit a dysregulation of the Hippo signalling pathway, such as with no limitation: lung cancer, such as for example, non-small cell lung cancer (NSCL), liver, prostate, colon, head and neck, ovary, brain and breast cancers, mesothelioma, leukemia, such as for example acute lymphoblastic leukemia, sarcomas, and melanomas, such as for example uveal melanoma (iris, ciliary body or choroid melanoma).

In some embodiments, the cancer is selected from the group consisting of non-small cell lung cancer (NSCL), ovarian cancer and melanomas, such as for example uveal melanoma.

Preferably, the peptide, polynucleotide, and/or vector as described herein are used as adjuvants in combination with another anti-tumor agent, surgery, and/or radiotherapy. The anti-tumor agent is preferably a chemotherapeutic agent, such as for example: (i) an inhibitor of DNA replication like DNA binding agents, in particular alkylating or intercalating drugs, (ii) an antimetabolite agent such as DNA polymerase inhibitors or Topoisomerase I or II inhibitors, or (iii) an anti-mitogenic agent such as alkaloids. Such examples of chemotherapeutic agents include with no limitations: 5-FU, Oxaliplatin, Cisplatin, Carboplatin, Irinotecan, Cetuximab, Erlotinib, Docetaxel, and Paclitaxel.

In some embodiments, a peptide comprising or consisting of SEQ ID NO: 2 or SEQ ID NO: 3, a functional variant thereof or a chimeric peptide derived therefrom, as described above is used in combination with a chemotherapeutic agent as defined above.

The invention relates also to a pharmaceutical composition, comprising a peptide, polynucleotide, and/or vector as described above, and a pharmaceutically acceptable carrier. Preferably, the composition further comprises another anti-tumor agent, more preferably a chemotherapeutic agent, as defined above.

The pharmaceutical composition is formulated for administration by a number of routes, including but not limited to oral, parenteral and local. The pharmaceutically acceptable carriers are those conventionally used.

The pharmaceutical composition comprises a therapeutically effective amount of the peptide/polynucleotide/vector, e.g., sufficient to show benefit to the individual to whom it is administered. The pharmaceutically effective dose depends upon the composition used, the route of administration, the type of mammal (human or animal) being treated, the physical characteristics of the specific mammal under consideration, concurrent medication, and other factors, that those skilled in the medical arts will recognize.

The invention provides also a method for treating a patient having a disease comprising a deregulation of the Hippo signalling pathway, comprising: administering a therapeutically effective amount of the peptide, polynucleotide and/or vector to the patient, preferably, in combination with another anti-tumor agent as defined above.

Another aspect of the invention relates to a combined preparation containing a peptide, polynucleotide, vector as described herein and an anti-tumor agent, for the simultaneous, separate or sequential use in the treatment of a hyperproliferative disease, in particular a cancer, preferably a cancer exhibiting a deregulation of the Hippo pathway as defined above.

The peptide for use in therapy is advantageously a peptide comprising or consisting of SEQ ID NO: 2, a functional variant thereof such as a variant comprising or consisting of SEQ ID NO:38, or a chimeric peptide derived therefrom such as SEQ ID NO: 36 or 39. Said peptide may be combined with at least another peptide according to the present invention, in particular a peptide comprising or consisting of SEQ ID NO: 3, a functional variant or a chimeric peptide derived therefrom such as SEQ ID NO: 37.

Another aspect of the invention is the use of the peptide inhibitor or derived chimeric peptide of the invention as reagent for in vitro diagnostic of diseases comprising a deregulation of the Hippo signalling pathway, as defined above.

Another aspect of the invention is the use of the peptide inhibitor or derived chimeric peptide of the invention as a research tool, in particular to study the Hippo signalling pathway.

Yet another aspect of the invention is the use of the peptide inhibitor derived chimeric peptide of the invention as reagent for drug screening, in particular for the screening of modulators of the Hippo signalling pathway.

The peptide for the diagnostic, drug screening and research uses is advantageously a labelled peptide, i.e., a peptide linked to a labeling agent which produces a detectable and/or quantifiable signal, in particular a radioactive, magnetic or luminescent agent.

The invention encompasses the use of a combination of at least two different peptides according to the present invention. In some embodiments a peptide comprising or consisting of SEQ ID NO: 2, a functional variant such as a variant comprising or consisting of SEQ ID NO:38 or a chimeric peptide derived therefrom such as SEQ ID NO: 36 or 39, is used in combination with a peptide comprising or consisting of SEQ ID NO: 3, a functional variant or a chimeric peptide derived therefrom such as SEQ ID NO: 37.

The peptide of the invention is prepared by the conventional techniques known to those skilled in the art. The peptide is usually solid-phase synthesized, according to the Fmoc technique, originally described by Merrifield et al. (J. Am. Chem. Soc., 1964, 85, 2149-) and purified by reverse-phase high performance liquid chromatography. Alternatively, the peptide is produced from the corresponding polynucleotide, usually a cDNA, obtained by any means known to those skilled in the art. For example, the polynucleotide is produced by amplification of a nucleic sequence by PCR or RT-PCR, by screening genomic DNA libraries by hybridization with a homologous probe, or else by total or partial chemical synthesis. Recombinant vectors are constructed and introduced into host cells by the conventional recombinant DNA and genetic engineering techniques, which are known in the art. The recombinant peptide produced in an appropriate cell system is purified by any suitable means, in particular by affinity chromatography.

The practice of the present invention will employ, unless otherwise indicated, conventional techniques which are within the skill of the art. Such techniques are explained fully in the literature.

In addition to the above arrangements, the invention also comprises other arrangements, which will emerge from the description which follows, which refers to exemplary embodiments of the subject of the present invention, with reference to the attached drawings in which:

FIG. 1 illustrates determination of the binding site of TEAD to YAP or TAZ and vice versa. A. Overlapping dodecapeptides with two amino acid shift covering the whole human TEAD protein were bound to a solid support. The membrane was incubated sequentially with YAP-GST protein, and anti-GST antibody, followed by a preoxydase-labeled secondary antibody. The membrane was revealed with ECL system. The sequence corresponding to the identified spots is shown. B. Overlapping dodecapeptides with two amino acid shift covering the whole human TEAD protein were bound to a solid support. The membrane was incubated sequentially with TAZ-GST protein, and anti-GST antibody, followed by a preoxydase-labeled secondary antibody. The membrane was revealed with ECL system. The sequence corresponding to the identified spots is shown. C. Overlapping dodecapeptides with two amino acids shift covering the YAP protein were synthesized and bound to a solid support. The membrane was incubated with TEAD-GST protein, followed by anti-GST antibody and a secondary peroxidase-conjugated antibody. The membrane was revealed using the ECL system. The sequence corresponding to the identified spots is shown.

Figure 2:
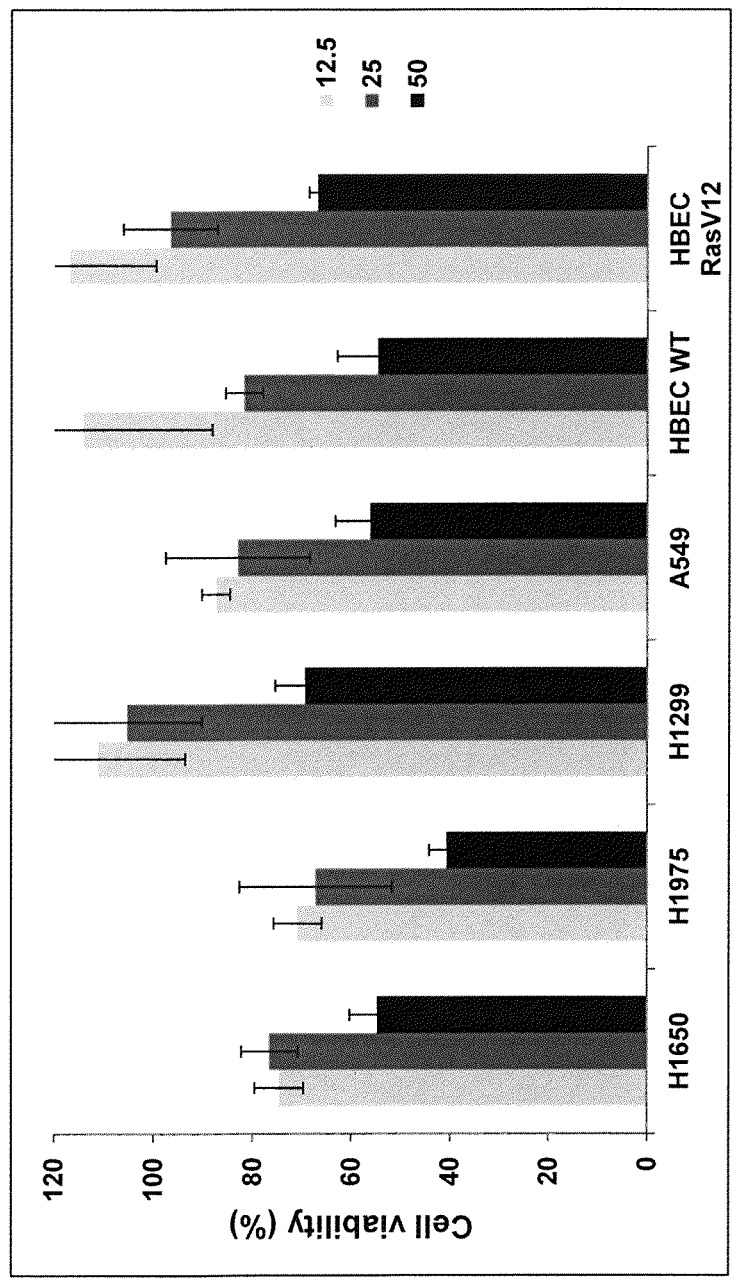

FIG. 2 illustrates cytotoxic effect of TEAD peptide in Non small cell lung cancer (NSLC) cell lines. NSCL cell lines were incubated for 72 h with different concentrations of TEAD peptide (12.5, 25 or 50 µM). Cytotoxicity was evaluated by MTT. Cell viability is presented relative to non-treated cells.

Figure 3:
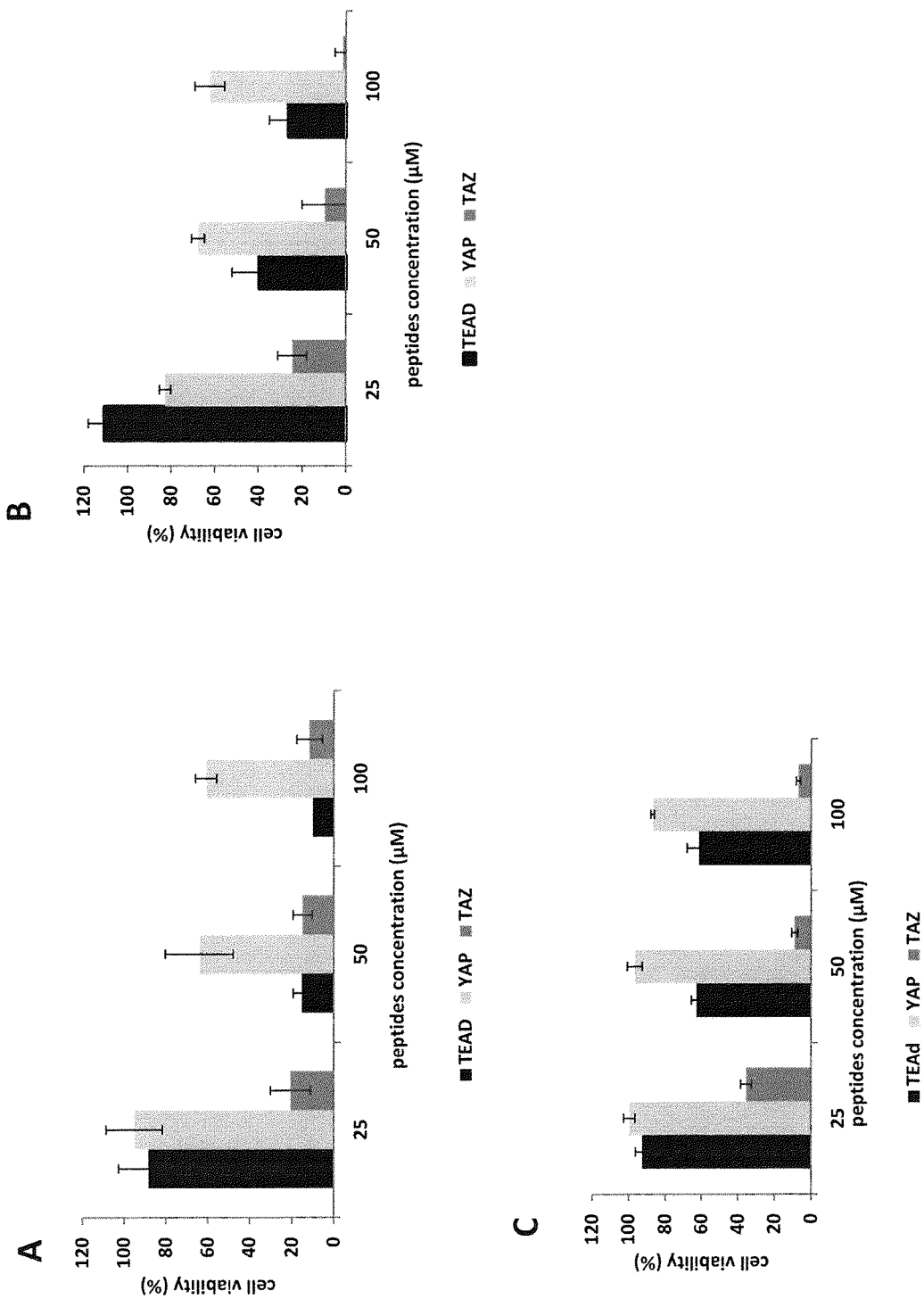

FIG. 3 illustrates cytotoxic effect of TEAD, YAP and TAZ peptides in human uveal melanoma cell lines. MP41, MP46 and MP66 cell lines were incubated for 72 h with different concentrations of peptides (25, 50 or 100 µM). Cytotoxicity was evaluated by MTT assay. Cell viability relative to non-treated cells is presented at the different concentrations of peptides. A. MP41 cells. B. MP46 cells. C. MP66 cells.

Figure 4:
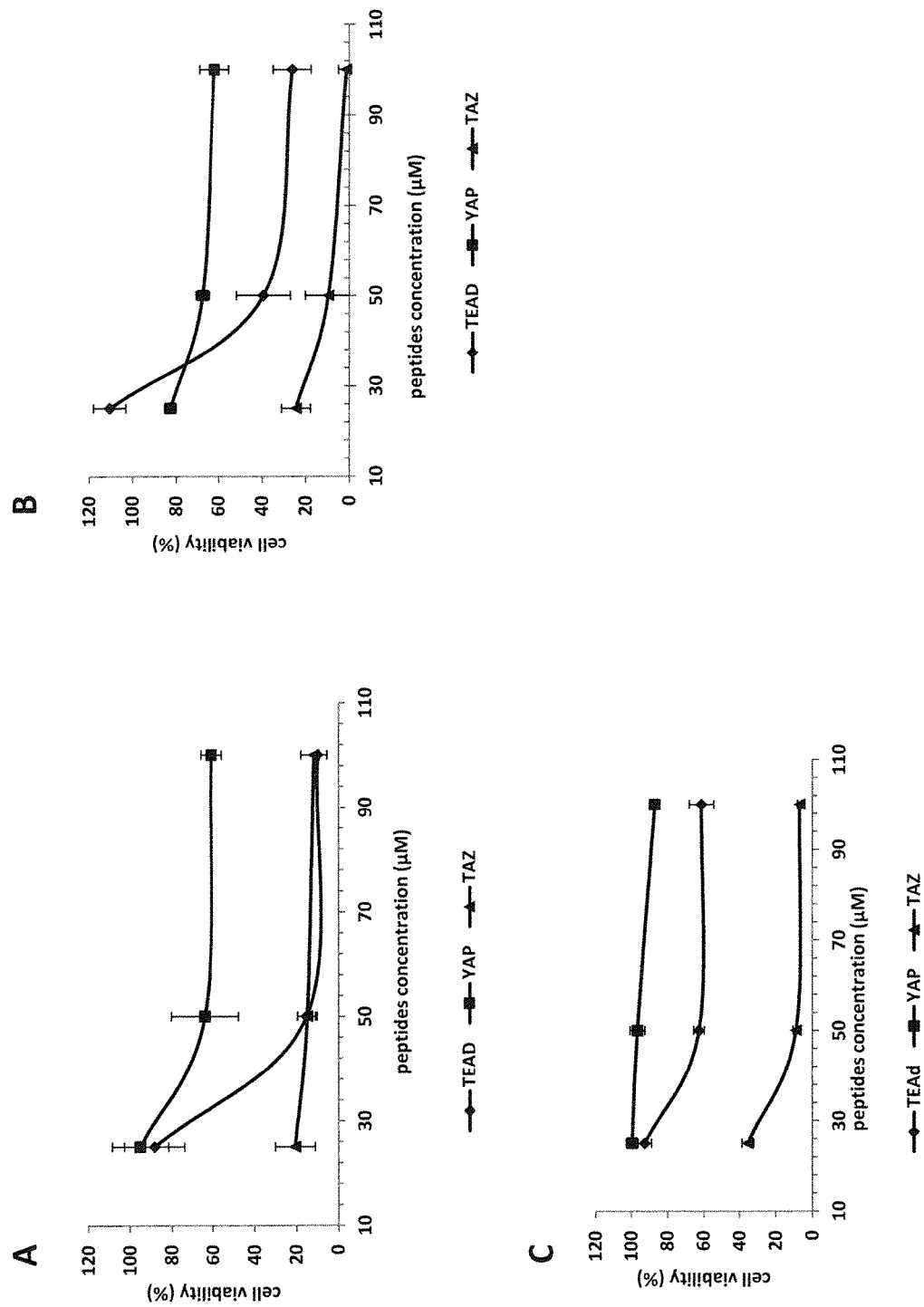

FIG. 4 illustrates cytotoxic effect of TEAD, YAP and TAZ peptides in human uveal melanoma cell lines. MP41, MP46 and MP66 cell lines were incubated for 72 h with different concentrations of peptides (25, 50 or 100 µM). Cytotoxicity was evaluated by MTT assay. Cell viability relative to non-treated cells is presented for increasing peptide concentrations (from 25 to 100 µM). A. MP41 cells+peptides. B. MP46 cells+peptides. C. MP66 cells+peptides.

Figure 5:
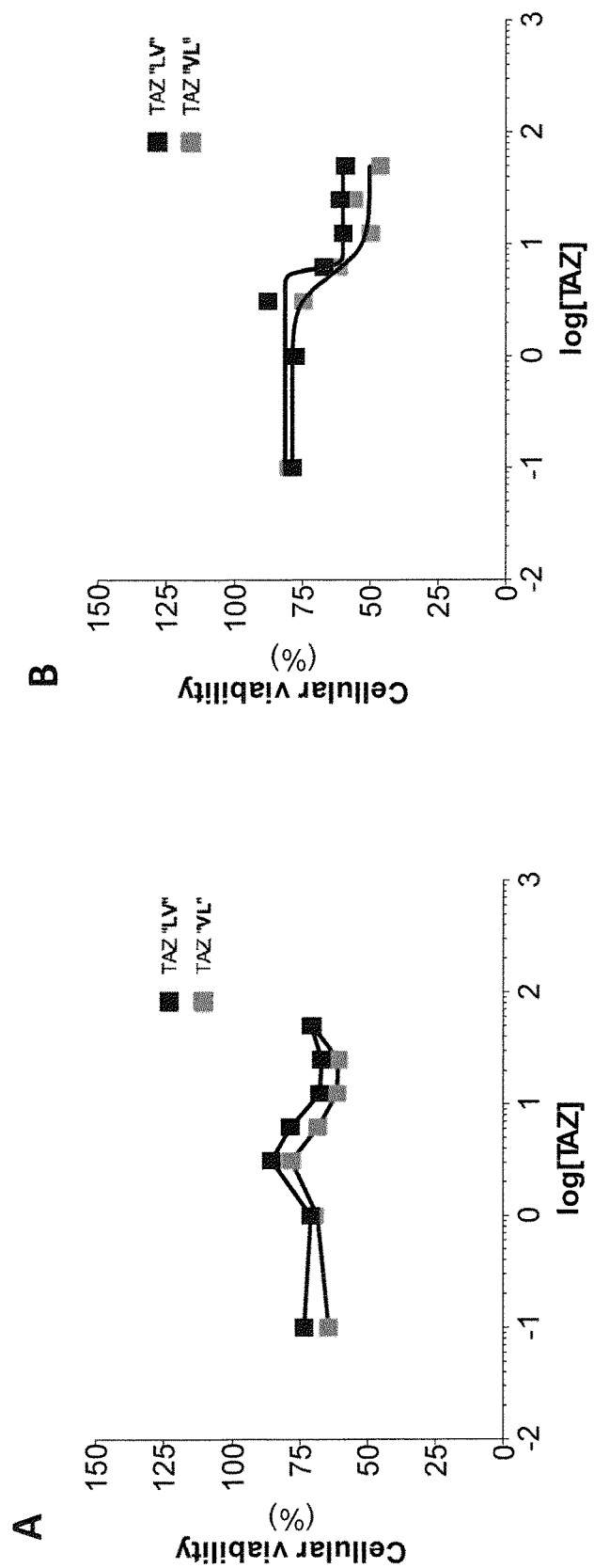

FIG. 5 illustrates cytotoxic effect of TAZ "LV" and "VL" peptides in human colon cancer cell lines. HCT116 and HT29 cell lines were incubated for 72 h with different concentrations of peptides. Cytotoxicity was evaluated by MTT assay. Cell viability relative to non-treated cells is presented for increasing peptide concentrations (0.1 to 100 µM). A. HCT116 cells. B. HT29 cells.

Figure 6:
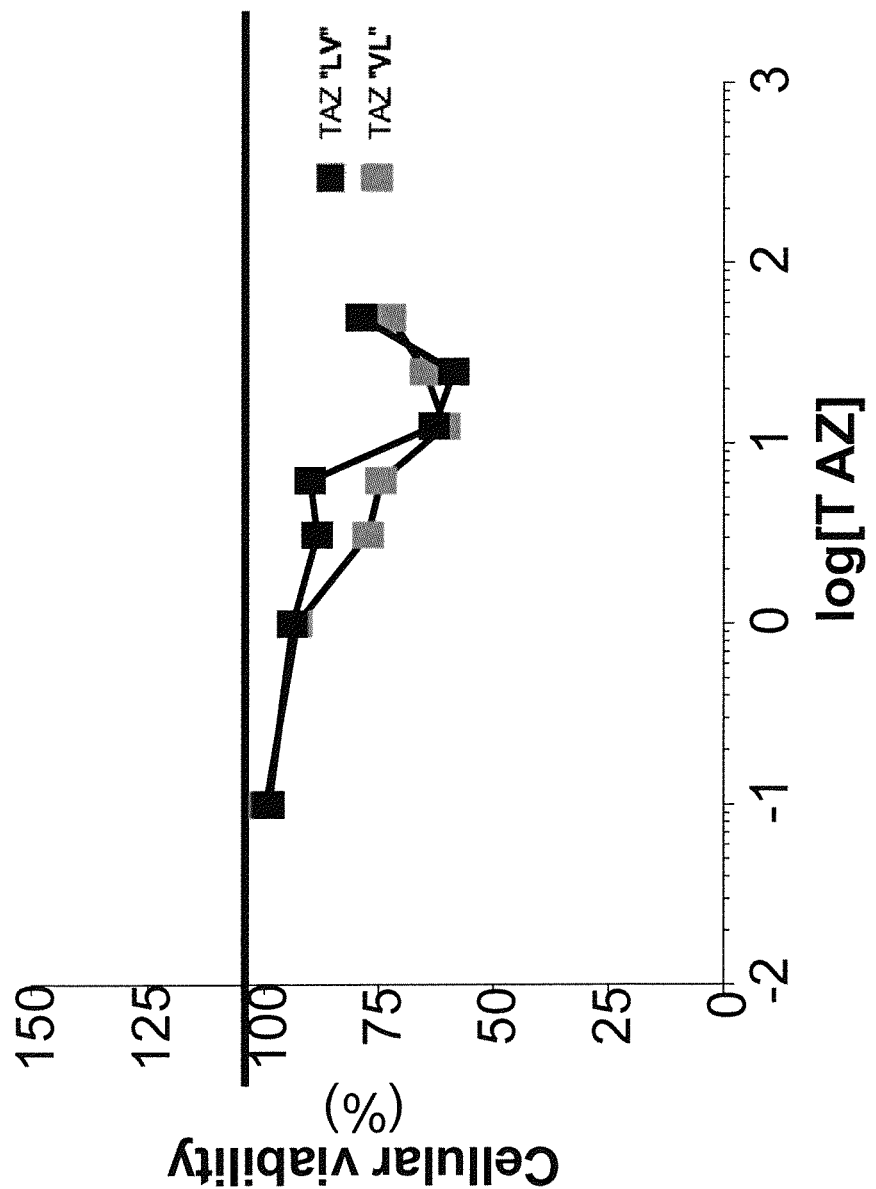

FIG. 6 illustrates cytotoxic effect of TAZ "LV" and "VL" peptides in human colon cancer cell line SW480. SW480 cell line was incubated for 72 h with different concentrations of peptides. Cytotoxicity was evaluated by MTT assay. Cell viability relative to non-treated cells is presented for increasing peptide concentrations (0.1 to 100 µM).

Figure 7:
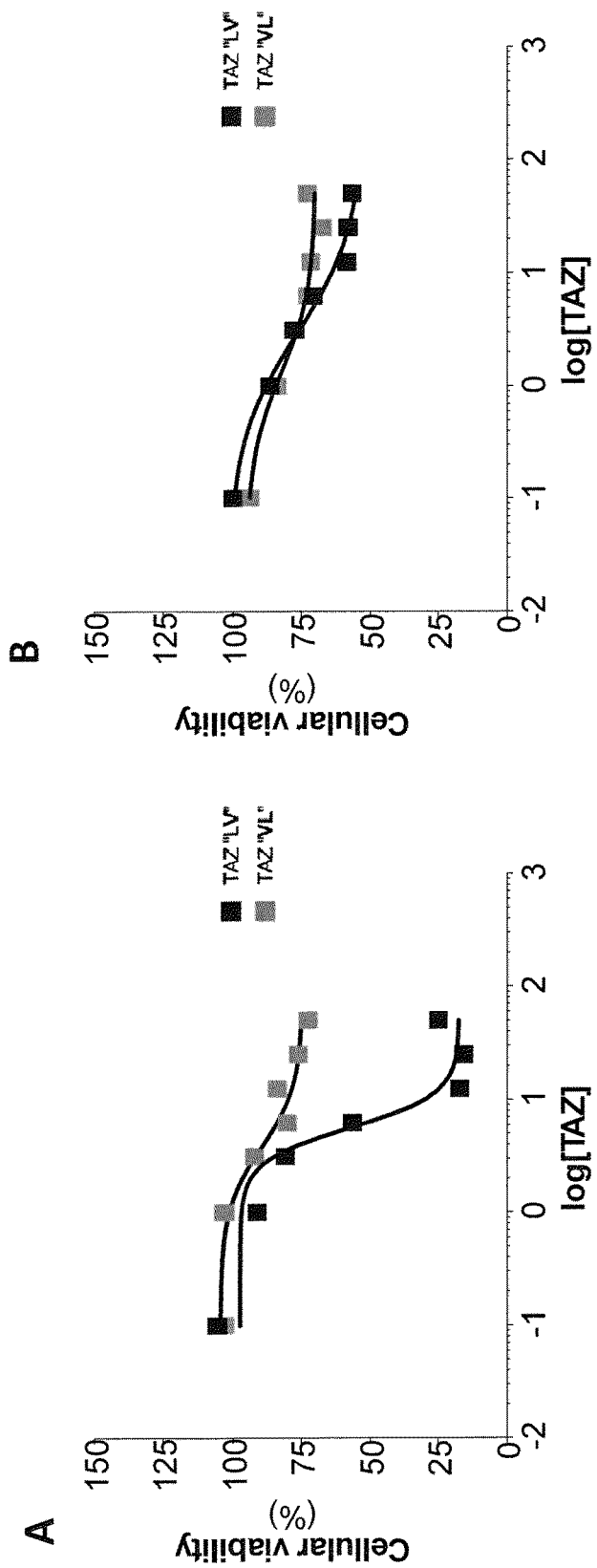

FIG. 7 illustrates cytotoxic effect of TAZ "LV" and "VL" peptides in human ovarian cancer cell lines. ES2 and OVCAR8 cell lines were incubated for 72 h with different concentrations of peptides. Cytotoxicity was evaluated by MTT assay. Cell viability relative to non-treated cells is presented for increasing peptide concentrations (0.1 to 100 µM)). A. ES2 cells. B. OVCAR8 cells.

Figure 8:
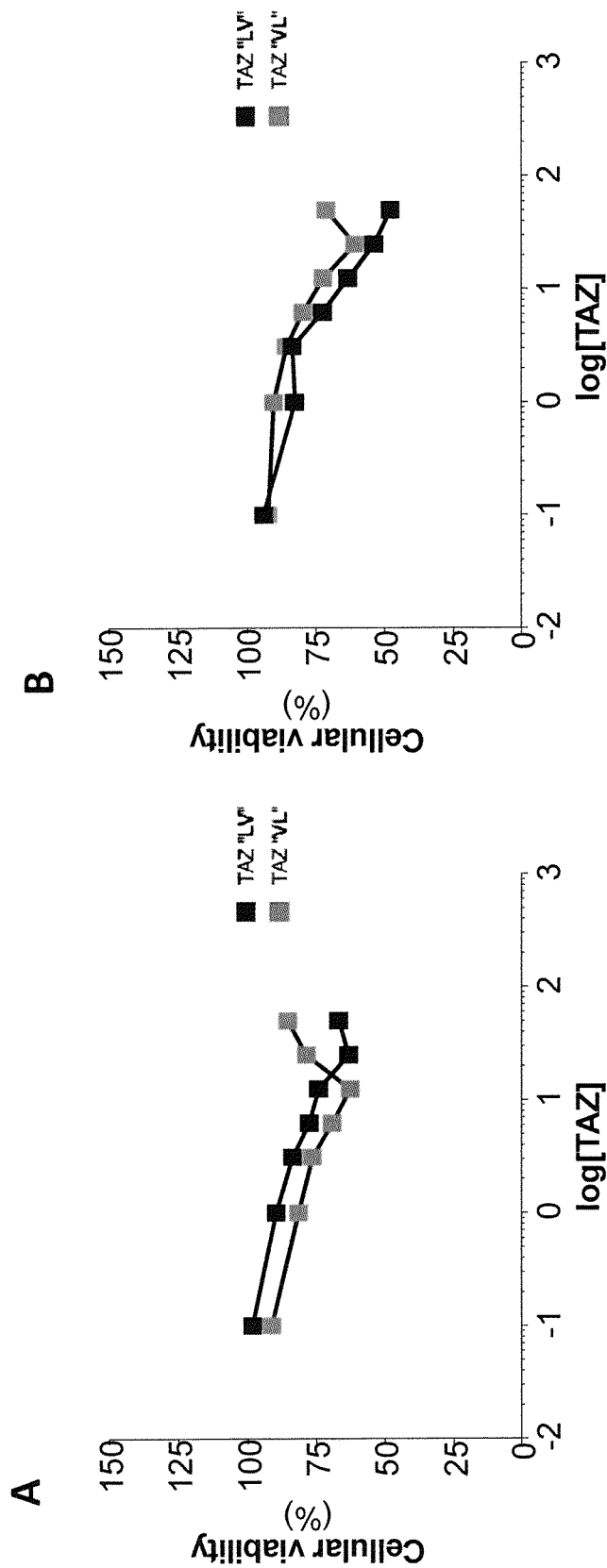

FIG. 8 illustrates cytotoxic effect of TAZ "LV" and "VL" peptides in human lung cancer cell lines. A549 and HT1975 cell lines were incubated for 72 h with different concentrations of peptides. Cytotoxicity was evaluated by MTT assay. Cell viability relative to non-treated cells is presented for increasing peptide concentrations (0.1 to 100 µM). A. A549 cells. B. HT1975 cells.

FIG. 9 presents Table III: Cytotoxicity of TAZ peptide in combination with chemotherapy.

FIG. 10 presents Table IV: Cytotoxicity of TEAD peptide in combination with chemotherapy.

FIG. 11 presents Table V: Cytotoxicity of YAP peptide in combination with chemotherapy.

FIG. 12 presents Table VI: Cytotoxicity of TAZ peptide in combination with YAP peptide.

FIG. 13 presents Table IX: Cytotoxicity of TAZ peptide in combination with chemotherapy.

EXAMPLE 1: IDENTIFICATION OF BINDING SITE OF TEAD TO YAP/TAZ AND VICE VERSA

1. Materials and Methods

Peptide Synthesis and Sequence

Peptides were synthesized in an automated multiple peptide synthesizer with solid phase procedure and standard Fmoc chemistry. The purity and composition of the peptides were confirmed by reverse phase HPLC and by amino acid analysis. These peptides were used for protein-protein interaction competition studies or cell culture.

TEAD/YAP-TAZ Binding Assay on Cellulose-Bound Peptides Containing TEAD, TAZ or YAP Sequences Overlapping peptides covering the human TEAD, TAZ or YAP proteins were prepared by automated spot synthesis into an amino-derivatized cellulose membrane as previously described (Frank R. and Overwin H., Methods Mol. Biol., 1996, 66, 149-169). The membranes were blocked, incubated with purified TEAD, YAP or TAZ protein and, after several washing steps, incubated with anti-TEAD, TAZ or YAP antibody tagged with GST followed by the PO-conjugated secondary Ab anti GST. Protein interactions were visualized using the ECL system.

2. Results

To identify peptides containing TEAD sequence able to bind to YAP, the whole sequence of TEAD was synthesized as series of dodecapeptides that were bound to a nitrocellulose support. One overlapping sequence of four dodecapeptides corresponding to the binding site of TEAD to YAP was identified (FIG. 1A). The sequence of 18 amino acids, denominated peptide TEAD, is: RLQLVEFSAFVEPPDAVD (SEQ ID NO: 1).

The membrane containing the TEAD sequence was in a second time hybridized with the TAZ protein. A sequence of 26 amino acids corresponding to the binding site of TEAD to TAZ was identified (FIG. 1B). The sequence, denominated peptide TAZ, is: PPHAFFLVKFWADLNWGPSGEEAGAG (SEQ ID NO: 2).

Figure 1C:
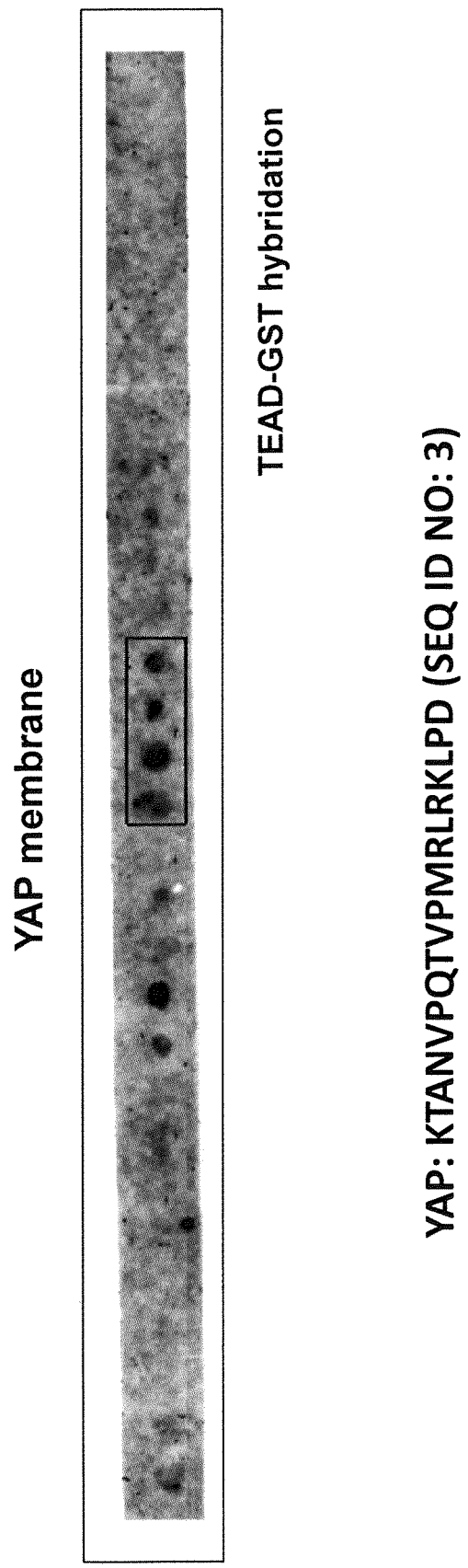

Similarly, to identify peptides containing YAP sequence able to bind to TEAD, the YAP protein was synthesized as series of dodecapeptides that were bound to a solid support. One binding site of YAP to TEAD was identified (FIG. 1C). The sequence, denominated peptide YAP, is: KTANVPQT-VPMRLRKLPD (SEQ ID NO: 3).

EXAMPLE 2: CYTOTOXICITY OF TAZ, YAP AND TEAD PEPTIDES IN HUMAN NON-SMALL CELL LUNG CANCER CELL LINES

1. Materials and Methods
Cells
H1650, H1975, H1299, A549 cell lines were cultured in DMEM medium supplemented with 10% of FCS. HBEC cell lines (wt and Ras V12) were cultured in KSFM supplemented with growth factors. All the cell lines come from human non small cell lung cancer (NSCLC).

TABLE I

Mutational status of the NSCLC cell lines

| Cell line | Pathology | Mutation |
|---|---|---|
| A549 | Carcinoma | K-Ras |
| H1299 | Non small cell lung Adenocarcinoma | EGFR wt N-Ras Partial P53 deletion |
| H1650 | Adenocarcinoma | EGFR |
| H1975 | Non small cell lung Adenocarcinoma | EGFR K-Ras P53 P16 P14 |
| HBEC wt | Human bronchial epithelial cell | P16 Rb |
| HBEC Ras V12 | Human bronchial epithelial cell | K-Ras P16 Rb |

Cell Penetrating Peptides
Cell-penetrating peptides (CPPs): TAZ "LV" (SEQ ID NO: 36), TAZ "VL" (SEQ ID NO: 39), TEAD (SEQ ID NO: 35) and YAP (SEQ ID NO: 37) were chemically synthesized as described in Example 1. These peptides are chimeric peptides corresponding to the binding site of TEAD to TAZ or YAP or of YAP to TEAD associated to the Mut3DPT-Sh1 shuttle (VKKKKIKAEIKI: SEQ ID NO: 9) described in WO 2013/098337.

Cytotoxicity Assay
The cytotoxicity of penetrating peptides or chemotherapeutic agents, alone or in combination, was evaluated by the (3-(4,5-dimethylthiazol-2-yl)-2,5-diphenyltetrazolium bromide) tetrazolium (MTT) reduction assay. The cells were seeded in 96-well plates (100 μL/well) at a cell density defined from growth curves. After 24 hours of incubation, cells were treated with the peptides for 72 hours. The wells were rinsed two times with RPMI. After washing, 10 μl of stock MTT solution (5 mg/ml; MTT (SIGMA #M-2128) in PBS Dubecco's 1× without $Ca^{2+}$ and $Mg^{2+}$) was added to a final volume of 100 μl of culture medium. Cell lines were incubated for additional 4 hours at 37° C. under humid atmosphere with 5% (v/v) $CO_2$. The formation of blue formazan crystals was detected under a microscope. An equal volume of 10% SDS (MERCK, #926.238) in 10 mM HCl was added to each well and the plate was placed in the incubator overnight to dissolve formazan crystals. The plates were mixed to ensure complete solubilisation of formazan crystals and absorbance was measured at 570 nm and 620 nm. The percentage of viable cells was estimated using the formula: % cell viability=$\Delta OD_{(570-620)}$ treated/$\Delta OD_{(570-620)}$control×100. The $LD_{25}$ (or $IC_{25}$) and $LD_{50}$ (or $IC_{50}$), corresponding to the concentrations causing 25% and 50% cell death, respectively, were determined.

Cytotoxic Agents
Cisplatin (small molecule; Antimetabolite); Docetaxel (Taxotere®; small molecule; microtubule hyper-stabilizer); Erlotinib (Tarceva™; EGFR tyrosine kinase inhibitor).

Statistical Analyses
All values are means+/−SEM. All experiments were replicated in triplicate. Data were analyzed by appropriate non-parametric Mann-Whitney (One-tailed) tests as indicated in the figure legends and tables, using GraphPad Prism® software. A p-value less than 0.05 was considered significant.

Synergistic, antagonist or additive effects in combination therapy were measured by the Combination Index (CI) using the CompuSyn software. If the CI value is equal to 1, additivity is indicated. If the CI value is <1, synergy is indicated, and if the CI value is >1, antagonism is indicated.

2. Results
Cell-penetrating peptides (CPPs) comprising the binding site of TEAD to TAZ or YAP or of YAP to TEAD (TAZ, TEAD and YAP peptides, respectively) were chemically synthesized. The effect of the peptides on cell viability was assayed on several human non small cell lung cancer (NSCLC) cell lines. All the lung cancer cell lines were treated for 72 h with different peptide concentrations. Cytotoxicity was analysed as described in Materials and Methods.

The $LD_{25}$ and $LD_{50}$ of the different peptides for the human non small cell lung cancer (NSCLC) cell lines are presented in Table II.

TABLE II

Cytotoxicity of the CPPs in NSCLC cell lines

| DRUGS | Letal Dose (μM) | A549 | H1299 | H1650 | H1975 | HBEC WT | HBEC RasV12 |
|---|---|---|---|---|---|---|---|
| TEAD | LD50 | >100 | >100 | 100 | 25 | >100 | >100 |
|  | LD25 | >100 | >100 | 5 | 6 | >100 | >100 |
| TAZ | LD50 | 50 | 10 | >100 | 6 | 1.5 | 1.5 |
|  | LD25 | 6 | 5 | >100 | 3 | 2.5 | 2.5 |
| YAP | LD50 | >100 | >100 | >100 | >100 | >100 | >100 |
|  | LD25 | >100 | >100 | >100 | >100 | >100 | >100 |
| Cisplatin | LD50 | 11 | 70 | 4 | 100 | 10 | 5 |
|  | LD25 | 3 | 30 | 2 | 30 | 2 | 1 |
| Docetaxel | LD50 | 0.001 | 0.013 | 0.0002 | 0.01 | 0.001 | 0.001 |
|  | LD25 | 0.0002 | 0.007 | 0.0001 | 0.0008 | 0.0002 | 0.0002 |

TABLE II-continued

Cytotoxicity of the CPPs in NSCLC cell lines

| DRUGS | Letal Dose (μM) | A549 | H1299 | H1650 | H1975 | HBEC WT | HBEC RasV12 |
|---|---|---|---|---|---|---|---|
| Tarceva | LD50 | 10 | >100 | 10 | 20 | 2 | 0.1 |
|  | LD25 | 0 | >100 | 0.4 | 3 | 0.04 | 0.001 |

LD25 of TAZ is significant for 5/6 cancer cell lines tested while no response was observed for YAP. TEAD has a slight effect only on H1650 and 1975 cell lines. TEAD peptide has a cytotoxic effect in H1650 and H1975 lung cancer cell lines at 12 and 25 μM. The cytotoxic effect increased with the TEAD peptide concentration of 50 μM (FIG. 2).

The CPPs were tested in NSCLC cell lines, in combination with chemotherapy (Table III to V).

TAZ was the most effective peptide in combination with chemotherapy in comparison to other Hippo CPPs on NSCLC cancer cell lines. Surprisingly, a slight response was observed with YAP in combination with other therapy.

Combinations of CPPs were also tested in NSCLC cell lines (Table VI).

Additive effect of TAZ and YAP was observed on NSCLC cancer cell lines. This effect is very important on HBEC WT/RasV12 cells.

EXAMPLE 3: CYTOTOXICITY OF TAZ, YAP AND TEAD PEPTIDES IN HUMAN OVARIAN CANCER CELL LINES

Materials and Methods
Cells
ES2, IGROV-1, OVCAR8 and SKOV3 cell lines come from human ovarian cancer.

TABLE VII

Human ovarian cancer cell lines

| Cell lines | Organism | Origin | Histology |
|---|---|---|---|
| ES2 | Homo sapiens, Human | Woman (African) 47 year old. | Poorly differentiated ovarian clear cell carcinoma |
| IGROV-1 | Homo sapiens, Human | Woman, 47 year old | Ovarian cancer of Stage III. Glandular and polymorphous ovarian epithelioma. |
| OVCAR8 | Homo sapiens, Human | Woman, 64 year old. | Carcinoma. |
| SKOV3 | Homo sapiens, Human | Woman (Caucasian), 64 year old | ND* |

*ND = Not Determined

Cell Penetrating Peptides
    See example 2
Cytotoxicity Assay
    See example 2
Cytotoxic Agents
    Carboplatin (small molecule; antimetabolite) and Paclitaxel (Taxol®; small molecule; microtubules hyperstabilizer).
Statistical Analysis
    See example 2
Results
    Cell-penetrating peptides (CPPs) comprising the binding site of TEAD to TAZ or YAP or of YAP to TEAD (TAZ, TEAD and YAP peptides, respectively) were chemically synthesized. The effect of the peptides on cell viability was assayed on several human ovarian cancer cell lines. All the ovarian cancer cell lines were treated for 72 h with different peptide concentrations. Cytotoxicity was analysed as described in example 2.

The $LD_{25}$ and $LD_{50}$ of the peptides TEAD, TAZ, "VL" and YAP (SEQ ID NO: 35, 37 and 39) for the human ovarian cancer cell lines are presented in Table VIII.

TABLE VIII

Cytotoxicity of the CPPs in ovarian cancer cell lines

| | | CELL LINES | | | |
|---|---|---|---|---|---|
| DRUGS | Letal Dose (μM) | ES2 | SKOV3 | IGROV | OVCAR8 |
| TEAD | LD50 | >100 | 25 | >100 | >100 |
|  | LD25 | >100 | 6 | >100 | >100 |
| TAZ | LD50 | 15 | >100 | 100 | 100 |
|  | LD25 | 6 | 60 | 5 | 9 |
| YAP | LD50 | >100 | >100 | >100 | >100 |
|  | LD25 | >100 | >100 | >100 | >100 |
| Carboplatin | LD50 | 25 | 45 | 65 | 110 |
|  | LD25 | 10 | 18 | 30 | 30 |
| Paclitaxel | LD50 | 0.004 | 0.010 | 0.004 | 0.001 |
|  | LD25 | 0.004 | 0.005 | 0.002 | 0.003 |

LD25 of TAZ is significant for 3/3 cancer cell lines tested while no response was observed for YAP. TEAD has a slight effect only on SKOV3 cells.

TAZ response is comparable to classically used Carboplatin in term of doses employed.

The CPPs were tested in ovarian cancer cell lines, in combination with chemotherapy (Table IX).

A better efficacy of combination therapy in comparison to chemotherapy alone was observed for 100% of ovarian cancer cell lines tested. A cytotoxic effect was only observed with combination of chemotherapy and TAZ therapy on ¾ ovarian cancer cell lines (ES2, IGROV and OVCAR8). A slight synergistic effect was observed between chemotherapy (Carboplatin and Paclitaxel) and TAZ on 2 ovarian cancer cell lines (ES2, SKOV3).

EXAMPLE 4: CYTOTOXICITY OF TAZ, YAP AND TEAD PEPTIDES IN HUMAN MELANOMA CELL LINES

Cells
    MP41, MP46 and MP66 cell lines come from uveal melanoma patient derived xenografts. They were cultured in RPMI medium supplemented with 20% of FCS.
Cell Penetrating Peptides
    See example 2
Cytotoxicity Assay
    See example 2
Statistical Analysis
    See example 2

Results

All the uveal melanoma cell lines were treated for 72 h with different concentrations of the peptides TAZ, "LV", YAP and TEAD (SEQ ID NO: 35, 36, 37). Cytotoxicity was analysed as described in example 2. As shown in FIGS. 3 and 4, TAZ "LV" is very efficient in these 3 cell lines, with about 20% of viability at 25 μM. TEAD showed cytotoxicity in MP41 and MP46 with IC50=35 and 44 μM respectively, but it is less efficient in MM66 with 60% of cytotoxicity at 100 μM. The peptide YAP showed less cytotoxic effect than the 2 other peptides. The best effect was shown in MP41 with about 40% cytotoxicity at 100 μM.

EXAMPLE 5: COMPARISON OF THE CYTOTOXIC EFFECT OF TAZ "LV" AND TAZ "VL" PEPTIDES

The effect of the TAZ "LV" (SEQ ID NO: 36) and TAZ "VL" (SEQ ID NO: 39) on lung, colon and ovarian cancer cell lines was assayed as described in example 2. The lung and ovarian cancer cell lines are described in examples 2, and 3, respectively.

TABLE X

Colon cancer cell lines

| Cell lines | Organism | Origin | Histology | Mutations |
|---|---|---|---|---|
| HCT116 | Homo sapiens | Male Adult | Colorectal carcinoma | K-Ras mut |
| HT29 | Homo sapiens | Woman (Caucasian) 44 year old | Colorectal carcinoma | |
| SW480 | Homo sapiens | Male (Caucasian) 50 year old | Dukes' type B, colorectal adenocarcinoma | K-Ras mut |

Both TAZ peptides have the same effect on cellular viability of all colon, lung and ovarian cancer cell lines tested, except for only one ovarian cancer cell line (ES2), in which TAZ "LV" is more effective than TAZ "VL" (FIGS. 5 to 8).

EXAMPLE 6: EVALUATION OF IN VIVO TOXICITY AND THERAPEUTIC EFFICACY OF THE CHIMERIC CELL-PENETRATING PEPTIDES IN PATIENT-DERIVED XENOGRAFTS MODELS

1. Determination of the Maximal Tolerable Doses of Chimeric CPPs Administered Alone, or in Combination with Chemotherapeutic Agents Six to eight weeks old Nude mice without transplanted tumors (n=3) were treated by intraperitoneal (IP) injection with chimeric CPPs alone or in combination with a chemotherapeutic agent, five days per week for one to four weeks. Four dose levels of chimeric CPPs were tested: 1, 5, 25 and 50 mg/kg per injection.

In NSCL, the chimeric CPPs were tested in combination with either, cisplatin (8 mg/kg, IP, day 1 and then every 3 weeks), docetaxel (20 mg/kg, IP, day 1 and then every 3 weeks), or cetuximab (40 mg/kg, IP, day 1 and then every 4 days).

In ovarian cancers, the chimeric CPPs were tested in combination with both carboplatin (66 mg/kg, IP, day 1 and then every 3 weeks) and paclitaxel (30 mg/kg, IP, day 1 and then every 3 weeks).

Moreover, each standard chemotherapeutic treatment was tested at full dose.

At day 1 of the next week, weights of individual mice were measured and variations of weight of mice as compared to their initial weight and means or median per group were calculated.

A treatment was considered as toxic in case of two or more deaths or in case of a one weight loss greater than 20% of the initial weight.

In the absence of death or weight loss greater than 10%, the dose was increased to the next level, using the same group of three mice.

In the presence of at least one death or one weight loss greater than 20%, the dose was considered to be toxic; a new group of three mice was then treated by intraperitoneal (IP) injection with a decreased dose corresponding to 50% of the toxic dose.

In the absence of death but weight loss between 10% and 20%, the dose was considered as potentially toxic; a new group of three mice was treated by intraperitoneal (IP) injection with the same dose.

When the maximal tolerable dose was determined according to this schedule, a validation was then performed in five Nude mice for four weeks.

At the end of the toxicity phase, therapeutic schedules were defined for further experiments.

2. Therapeutic Assays

Six to eight weeks old Nude mice weighing at least 18 g received a subcutaneous graft of tumor fragments with a volume of approximately 15 mm$^3$, according to the previously described in vivo models of primary human tumor xenografts (Némati et al., Anticancer Drugs, 2010, 21, 25-32; Némati et al., Anticancer Drugs, 2009, 10, 932-940).

The transplanted mice (n=12) were then treated by intraperitoneal (IP) injection with either chimeric CPPs alone, chimeric CPPs in combination with chemotherapeutic agent(s), or chemotherapeutic agent(s) alone, according to the intraperitoneal schedule of administration defined above; an untreated control group was included for comparison.

Tumour volume was calculated by measuring two perpendicular diameters with calipers. Each tumour volume (v) was calculated according to the following formulae: V=a×b$^2$/2, where a and b are the largest and the smallest perpendicular tumour diameters.

Relative tumour volume (RTV) was calculated from the following formula: RTV=(Vx/V1)×100, where Vx is the tumour volume on day X and V1 is the tumour volume at initiation of the therapy (day 1). These data allow to rapidly evaluate the lack of growth when the RTV is equal or under 100% (tumor regressions). Growth curves were obtained by plotting the mean (or median) volume of RTV on Y axis against time (X axis, expressed as days after starting of treatment), in treated group and control.

Antitumor activity was evaluated according to tumour growth-inhibition (TGI), calculated according to the following formulae: percent GI=100-(RTVt/RTVc)×100, where RTVt is the medium RTV of treated mice and RTVc is the median RTV of controls, both at a given time point when the anti-tumour effect was optimal.

Growth delay was calculated as the time in days necessary to multiply by four an initial tumor volume of 200 mm$^3$ in treated group and control group.

Weights of individual mice will be measured once a week. Variations of weight of mice as compared to their initial weight and means (or median) per group were calculated.

At the end of treatment, autopsy was performed for placebo or treatment groups and tumours were counted. Results are expressed as tumour number/mouse, mean±SEM.

All statistical tests were performed using Statview software. The following parameters were compared: tumor volume and/or RTV, optimal growth inhibition, growth delay, body weight change. Statistical analysis of the efficacy of the treatment was performed either by paired or unpaired t-test.

3. Pharmacodynamic Assays

Tumor samples of at least five treated mice per group were collected at the end of treatments; one part of each tumor was frozen for RT-PCRs and western blots, the other part was fixed in AFA (formaldehyde-acetic acid-alcohol) and embedded in paraffin for immunohistochemical studies.

Histopathological study included YAP and TEAD protein expression, in particular cytoplasmic and nuclear localization of YAP was assessed. RT-PCRs of genes whose expression is modulated by TEAD/Yap complex such as Ctgf, β2integrin, Areg, and Birc5 were also performed.

The invention claimed is:

1. A chimeric peptide, which comprises or consists of an amino acid sequence selected from SEQ ID NO: 35, SEQ ID NO: 36, SEQ NO: 37, and SEQ ID NO: 39.

2. A pharmaceutical composition comprising the chimeric peptide of claim 1.

* * * * *

```
                        SEQUENCE LISTING

<160> NUMBER OF SEQ ID NOS: 39

<210> SEQ ID NO 1
<211> LENGTH: 18
<212> TYPE: PRT
<213> ORGANISM: artificial sequence
<220> FEATURE:
<223> OTHER INFORMATION: synthetic peptide TEAD

<400> SEQUENCE: 1

Arg Leu Gln Leu Val Glu Phe Ser Ala Phe Val Glu Pro Pro Asp Ala
1               5                   10                  15

Val Asp

<210> SEQ ID NO 2
<211> LENGTH: 26
<212> TYPE: PRT
<213> ORGANISM: artificial sequence
<220> FEATURE:
<223> OTHER INFORMATION: synthetic peptide TAZ

<400> SEQUENCE: 2

Pro Pro His Ala Phe Phe Leu Val Lys Phe Trp Ala Asp Leu Asn Trp
1               5                   10                  15

Gly Pro Ser Gly Glu Glu Ala Gly Ala Gly
            20                  25

<210> SEQ ID NO 3
<211> LENGTH: 18
<212> TYPE: PRT
<213> ORGANISM: artificial sequence
<220> FEATURE:
<223> OTHER INFORMATION: synthetic peptide YAP

<400> SEQUENCE: 3

Lys Thr Ala Asn Val Pro Gln Thr Val Pro Met Arg Leu Arg Lys Leu
1               5                   10                  15

Pro Asp

<210> SEQ ID NO 4
<211> LENGTH: 11
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (1)..(1)
<223> OTHER INFORMATION: X is K, VK or is absent
<220> FEATURE:
<221> NAME/KEY: VARIANT
<222> LOCATION: (7)..(7)
<223> OTHER INFORMATION: X is any amino acid
```

```
<220> FEATURE:
<221> NAME/KEY: VARIANT
<222> LOCATION: (10)..(10)
<223> OTHER INFORMATION: X is  K, KI or is absent
<220> FEATURE:
<221> NAME/KEY: VARIANT
<222> LOCATION: (11)..(11)
<223> OTHER INFORMATION: X is a sequence of 1 to 4 amino acids or is
      absent

<400> SEQUENCE: 4

Xaa Lys Lys Lys Ile Lys Xaa Glu Ile Xaa Xaa
1               5                   10

<210> SEQ ID NO 5
<211> LENGTH: 10
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (1)..(1)
<223> OTHER INFORMATION: X is K, VK or is absent
<220> FEATURE:
<221> NAME/KEY: VARIANT
<222> LOCATION: (7)..(7)
<223> OTHER INFORMATION: X is any amino acid
<220> FEATURE:
<221> NAME/KEY: VARIANT
<222> LOCATION: (10)..(10)
<223> OTHER INFORMATION: X is K, KI or is absent

<400> SEQUENCE: 5

Xaa Lys Lys Lys Ile Lys Xaa Glu Ile Xaa
1               5                   10

<210> SEQ ID NO 6
<211> LENGTH: 12
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (8)..(8)
<223> OTHER INFORMATION: X is any amino acid

<400> SEQUENCE: 6

Val Lys Lys Lys Lys Ile Lys Xaa Glu Ile Lys Ile
1               5                   10

<210> SEQ ID NO 7
<211> LENGTH: 12
<212> TYPE: PRT
<213> ORGANISM: artificial sequence
<220> FEATURE:
<223> OTHER INFORMATION: synthetic peptide

<400> SEQUENCE: 7

Val Lys Lys Lys Lys Ile Lys Arg Glu Ile Lys Ile
1               5                   10

<210> SEQ ID NO 8
<211> LENGTH: 12
<212> TYPE: PRT
<213> ORGANISM: artificial sequence
<220> FEATURE:
<223> OTHER INFORMATION: synthetic peptide

<400> SEQUENCE: 8
```

Val Lys Lys Lys Lys Ile Lys Asn Glu Ile Lys Ile
1               5                   10

<210> SEQ ID NO 9
<211> LENGTH: 12
<212> TYPE: PRT
<213> ORGANISM: artificial sequence
<220> FEATURE:
<223> OTHER INFORMATION: synthetic peptide

<400> SEQUENCE: 9

Val Lys Lys Lys Lys Ile Lys Ala Glu Ile Lys Ile
1               5                   10

<210> SEQ ID NO 10
<211> LENGTH: 12
<212> TYPE: PRT
<213> ORGANISM: artificial sequence
<220> FEATURE:
<223> OTHER INFORMATION: synthetic peptide

<400> SEQUENCE: 10

Val Lys Lys Lys Lys Ile Lys Lys Glu Ile Lys Ile
1               5                   10

<210> SEQ ID NO 11
<211> LENGTH: 18
<212> TYPE: PRT
<213> ORGANISM: artificial sequence
<220> FEATURE:
<223> OTHER INFORMATION: synthetic peptide

<400> SEQUENCE: 11

Arg Gln Lys Arg Leu Ile Arg Gln Lys Arg Leu Ile Arg Gln Lys Arg
1               5                   10                  15

Leu Ile

<210> SEQ ID NO 12
<211> LENGTH: 18
<212> TYPE: PRT
<213> ORGANISM: artificial sequence
<220> FEATURE:
<223> OTHER INFORMATION: synthetic peptide

<400> SEQUENCE: 12

Arg His Ser Arg Ile Gly Arg His Ser Arg Ile Gly Arg His Ser Arg
1               5                   10                  15

Ile Gly

<210> SEQ ID NO 13
<211> LENGTH: 16
<212> TYPE: PRT
<213> ORGANISM: artificial sequence
<220> FEATURE:
<223> OTHER INFORMATION: synthetic peptide

<400> SEQUENCE: 13

Arg His Ser Arg Ile Gly Ile Ile Gln Gln Arg Arg Thr Arg Asn Gly
1               5                   10                  15

<210> SEQ ID NO 14
<211> LENGTH: 16
<212> TYPE: PRT
<213> ORGANISM: artificial sequence
<220> FEATURE:

<223> OTHER INFORMATION: synthetic peptide

<400> SEQUENCE: 14

Arg His Ser Arg Ile Gly Val Thr Arg Gln Arg Arg Ala Arg Asn Gly
1               5                   10                  15

<210> SEQ ID NO 15
<211> LENGTH: 15
<212> TYPE: PRT
<213> ORGANISM: artificial sequence
<220> FEATURE:
<223> OTHER INFORMATION: synthetic peptide

<400> SEQUENCE: 15

Arg Arg Arg Arg Arg Arg Arg Ser Arg Gly Arg Arg Arg Thr Tyr
1               5                   10                  15

<210> SEQ ID NO 16
<211> LENGTH: 9
<212> TYPE: PRT
<213> ORGANISM: artificial sequence
<220> FEATURE:
<223> OTHER INFORMATION: synthetic peptide

<400> SEQUENCE: 16

Arg Lys Lys Arg Arg Gln Arg Arg Arg
1               5

<210> SEQ ID NO 17
<211> LENGTH: 11
<212> TYPE: PRT
<213> ORGANISM: artificial sequence
<220> FEATURE:
<223> OTHER INFORMATION: synthetic peptide

<400> SEQUENCE: 17

Tyr Gly Arg Lys Lys Arg Arg Gln Arg Arg Arg
1               5                   10

<210> SEQ ID NO 18
<211> LENGTH: 9
<212> TYPE: PRT
<213> ORGANISM: artificial sequence
<220> FEATURE:
<223> OTHER INFORMATION: synthetic peptide

<400> SEQUENCE: 18

Arg Arg Arg Arg Arg Arg Arg Arg Arg
1               5

<210> SEQ ID NO 19
<211> LENGTH: 11
<212> TYPE: PRT
<213> ORGANISM: artificial sequence
<220> FEATURE:
<223> OTHER INFORMATION: synthetic peptide

<400> SEQUENCE: 19

Arg Arg Arg Arg Arg Arg Arg Arg Arg Arg
1               5                   10

<210> SEQ ID NO 20
<211> LENGTH: 32
<212> TYPE: PRT
<213> ORGANISM: artificial sequence
<220> FEATURE:
<223> OTHER INFORMATION: synthetic peptide

<400> SEQUENCE: 20

Gly Leu Phe Glu Ala Ile Glu Gly Phe Ile Glu Asn Gly Trp Glu Gly
1               5                   10                  15

Met Ile Asp Gly Trp Tyr Gly Arg Arg Arg Arg Arg Arg Arg Arg
            20                  25                  30

<210> SEQ ID NO 21
<211> LENGTH: 16
<212> TYPE: PRT
<213> ORGANISM: artificial sequence
<220> FEATURE:
<223> OTHER INFORMATION: synthetic peptide

<400> SEQUENCE: 21

Arg Gln Ile Lys Ile Trp Phe Gln Asn Arg Arg Met Lys Trp Lys Lys
1               5                   10                  15

<210> SEQ ID NO 22
<211> LENGTH: 27
<212> TYPE: PRT
<213> ORGANISM: artificial sequence
<220> FEATURE:
<223> OTHER INFORMATION: synthetic peptide

<400> SEQUENCE: 22

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 23
<211> LENGTH: 33
<212> TYPE: PRT
<213> ORGANISM: artificial sequence
<220> FEATURE:
<223> OTHER INFORMATION: synthetic peptide

<400> SEQUENCE: 23

Gly Asp Cys Leu Pro His Leu Lys Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg

<210> SEQ ID NO 24
<211> LENGTH: 10
<212> TYPE: PRT
<213> ORGANISM: artificial sequence
<220> FEATURE:
<223> OTHER INFORMATION: synthetic peptide

<400> SEQUENCE: 24

Lys Lys Lys Lys Lys Lys Lys Lys Lys Lys
1               5                   10

<210> SEQ ID NO 25
<211> LENGTH: 11
<212> TYPE: PRT
<213> ORGANISM: artificial sequence
<220> FEATURE:
<223> OTHER INFORMATION: synthetic peptide

<400> SEQUENCE: 25

```
Tyr Ala Arg Ala Ala Ala Arg Gln Ala Arg Ala
1               5                   10

<210> SEQ ID NO 26
<211> LENGTH: 12
<212> TYPE: PRT
<213> ORGANISM: artificial sequence
<220> FEATURE:
<223> OTHER INFORMATION: synthetic peptide

<400> SEQUENCE: 26

Pro Leu Ser Ser Ile Phe Ser Arg Ile Gly Asp Pro
1               5                   10

<210> SEQ ID NO 27
<211> LENGTH: 27
<212> TYPE: PRT
<213> ORGANISM: artificial sequence
<220> FEATURE:
<223> OTHER INFORMATION: synthetic peptide

<400> SEQUENCE: 27

Met Ala Asn Leu Gly Tyr Trp Leu Leu Ala Leu Phe Val Met Trp Thr
1               5                   10                  15

Asp Val Gly Leu Cys Lys Lys Arg Pro Lys Pro
            20                  25

<210> SEQ ID NO 28
<211> LENGTH: 35
<212> TYPE: PRT
<213> ORGANISM: artificial sequence
<220> FEATURE:
<223> OTHER INFORMATION: synthetic peptide

<400> SEQUENCE: 28

Gly Gly Gly Ala Arg Lys Lys Ala Ala Lys Ala Ala Arg Lys Lys Ala
1               5                   10                  15

Ala Lys Ala Ala Arg Lys Lys Ala Ala Lys Ala Ala Arg Lys Lys Ala
            20                  25                  30

Ala Lys Ala
        35

<210> SEQ ID NO 29
<211> LENGTH: 19
<212> TYPE: PRT
<213> ORGANISM: artificial sequence
<220> FEATURE:
<223> OTHER INFORMATION: synthetic peptide

<400> SEQUENCE: 29

Leu Leu Ile Ile Leu Arg Arg Arg Arg Ile Arg Lys Gln Ala His Ala
1               5                   10                  15

His Ser Lys

<210> SEQ ID NO 30
<211> LENGTH: 23
<212> TYPE: PRT
<213> ORGANISM: artificial sequence
<220> FEATURE:
<223> OTHER INFORMATION: synthetic peptide

<400> SEQUENCE: 30

Leu Ile Arg Leu Trp Ser His Leu Ile His Ile Trp Phe Gln Asn Arg
1               5                   10                  15
```

Arg Leu Lys Trp Lys Lys Lys
            20

<210> SEQ ID NO 31
<211> LENGTH: 22
<212> TYPE: PRT
<213> ORGANISM: artificial sequence
<220> FEATURE:
<223> OTHER INFORMATION: synthetic peptide

<400> SEQUENCE: 31

Thr Pro Trp Trp Arg Leu Trp Thr Lys Trp His His Lys Arg Arg Asp
1               5                   10                  15

Leu Pro Arg Lys Pro Glu
            20

<210> SEQ ID NO 32
<211> LENGTH: 20
<212> TYPE: PRT
<213> ORGANISM: artificial sequence
<220> FEATURE:
<223> OTHER INFORMATION: synthetic peptide

<400> SEQUENCE: 32

Gly Leu Trp Arg Ala Leu Trp Arg Leu Leu Arg Ser Leu Trp Arg Leu
1               5                   10                  15

Leu Trp Arg Ala
            20

<210> SEQ ID NO 33
<211> LENGTH: 23
<212> TYPE: PRT
<213> ORGANISM: artificial sequence
<220> FEATURE:
<223> OTHER INFORMATION: synthetic peptide

<400> SEQUENCE: 33

Asp Ser His Ala Lys Arg His His Gly Tyr Arg Lys Phe His Glu Lys
1               5                   10                  15

His His Ser His Arg Gly Tyr
            20

<210> SEQ ID NO 34
<211> LENGTH: 16
<212> TYPE: PRT
<213> ORGANISM: artificial sequence
<220> FEATURE:
<223> OTHER INFORMATION: synthetic peptide

<400> SEQUENCE: 34

Lys Lys Lys Glu Glu Arg Ala Asp Leu Ile Ala Tyr Leu Lys Lys Ala
1               5                   10                  15

<210> SEQ ID NO 35
<211> LENGTH: 30
<212> TYPE: PRT
<213> ORGANISM: artificial sequence
<220> FEATURE:
<223> OTHER INFORMATION: synthetic peptide

<400> SEQUENCE: 35

Val Lys Lys Lys Lys Ile Lys Ala Glu Ile Lys Ile Arg Leu Gln Leu
1               5                   10                  15

Val Glu Phe Ser Ala Phe Val Glu Pro Pro Asp Ala Val Asp
            20                  25                  30

```
<210> SEQ ID NO 36
<211> LENGTH: 38
<212> TYPE: PRT
<213> ORGANISM: artificial sequence
<220> FEATURE:
<223> OTHER INFORMATION: synthetic peptide

<400> SEQUENCE: 36

Val Lys Lys Lys Lys Ile Lys Ala Glu Ile Lys Ile Pro Pro His Ala
1               5                   10                  15

Phe Phe Leu Val Lys Phe Trp Ala Asp Leu Asn Trp Gly Pro Ser Gly
            20                  25                  30

Glu Glu Ala Gly Ala Gly
        35

<210> SEQ ID NO 37
<211> LENGTH: 30
<212> TYPE: PRT
<213> ORGANISM: artificial sequence
<220> FEATURE:
<223> OTHER INFORMATION: synthetic peptide

<400> SEQUENCE: 37

Val Lys Lys Lys Lys Ile Lys Ala Glu Ile Lys Ile Lys Thr Ala Asn
1               5                   10                  15

Val Pro Gln Thr Val Pro Met Arg Leu Arg Lys Leu Pro Asp
            20                  25                  30

<210> SEQ ID NO 38
<211> LENGTH: 26
<212> TYPE: PRT
<213> ORGANISM: artificial sequence
<220> FEATURE:
<223> OTHER INFORMATION: synthetic peptide

<400> SEQUENCE: 38

Pro Pro His Ala Phe Phe Val Leu Lys Phe Trp Ala Asp Leu Asn Trp
1               5                   10                  15

Gly Pro Ser Gly Glu Glu Ala Gly Ala Gly
            20                  25

<210> SEQ ID NO 39
<211> LENGTH: 38
<212> TYPE: PRT
<213> ORGANISM: artificial sequence
<220> FEATURE:
<223> OTHER INFORMATION: synthetic peptide

<400> SEQUENCE: 39

Val Lys Lys Lys Lys Ile Lys Ala Glu Ile Lys Ile Pro Pro His Ala
1               5                   10                  15

Phe Phe Val Leu Lys Phe Trp Ala Asp Leu Asn Trp Gly Pro Ser Gly
            20                  25                  30

Glu Glu Ala Gly Ala Gly
        35
```